United States Patent [19]

Plath et al.

[11] 4,316,039

[45] Feb. 16, 1982

[54] SUBSTITUTED 3-AMINOPYRAZOLES

[75] Inventors: Peter Plath, Ludwigshafen; Bruno Wuerzer, Limburgerhof; Wolfgang Rohr, Mannheim, all of Fed. Rep. of Germany

[73] Assignee: BASF Aktiengesellschaft, Fed. Rep. of Germany

[21] Appl. No.: 180,950

[22] Filed: Aug. 25, 1980

Related U.S. Application Data

[62] Division of Ser. No. 951,566, Oct. 16, 1978, Pat. No. 4,260,775.

[30] Foreign Application Priority Data

Oct. 22, 1977 [DE]  Fed. Rep. of Germany ....... 2747531

[51] Int. Cl.$^3$ ............................................ C07D 231/38

[52] U.S. Cl. .................................. 548/362; 548/377; 548/104; 548/360; 548/336; 548/262; 544/58.5; 544/60; 544/140; 544/371; 546/211; 546/279; 260/245.6

[58] Field of Search ............................. 548/362, 377

[56] References Cited

FOREIGN PATENT DOCUMENTS 2558117  7/1977  Fed. Rep. of Germany .

OTHER PUBLICATIONS

Beyer et al., Annalen, 1970, vol. 741, pp. 45–54.
Bulka et al., Chem. Berichte, 1965, vol. 98, pp. 259–273.

*Primary Examiner*—John M. Ford
*Assistant Examiner*—Natalia Harkaway
*Attorney, Agent, or Firm*—Keil & Witherspoon

[57] ABSTRACT

New and valuable pyrazole derivatives having a good herbicidal action, herbicides containing these compounds as active ingredients, and processes for controlling the growth of unwanted plants with these compounds.

1 Claim, No Drawings

SUBSTITUTED 3-AMINOPYRAZOLES

This is a division, of application Ser. No. 951,566, filed Oct. 16, 1978, now U.S. Pat. No. 4,260,775.

The present invention relates to new and valuable pyrazole derivatives having a good herbicidal action, herbicides containing these compounds as active ingredients, and processes for controlling the growth of unwanted plants with these compounds.

It is known that substituted pyrazoles or pyrazolium salts, e.g. 1,2-dimethyl-3,5-diphenylpyrazolium methyl sulfate, can be used as herbicides (German Laid-Open Applications DOS Nos. 2,513,750 and 2,260,485). It is also known that 2-(1-methyl-n-propyl)-4,6-dinitrophenyl acetate (German 1,088,575) or 3-isopropyl-2,1,3-benzothiadiazin-4-on-2,2-dioxide (German 1,542,836) may be used as herbicides.

We have now found that substituted pyrazoles of formula (1)

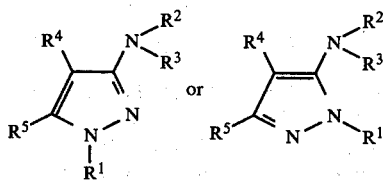

where $R^1$ denotes hydrogen or lower, unsubstituted or substituted alkyl or acyl, or cyano, alkoxycarbonyl, alkylaminocarbonyl, alkylaminothiocarbonyl, dialkylaminocarbonyl, dialkylaminothiocarbonyl, unsubstituted or substituted benzoyl, alkylsulfonyl, unsubstituted or substituted phenylsulfonyl, unsubstituted or substituted aryloxycarbonyl, arylamino-(thio)-carbonyl or alkylaminosulfonyl, $R^2$ denotes hydrogen or lower unsubstituted or alkoxy-substituted alkyl, or acyl, $R^3$ denotes unsubstituted alkyl or alkyl substituted by alkoxy, alkylthio, alkoxycarbonyl, cyano, halogen, aryl or a heterocyclic radical, or $R^3$ denotes cycloalkyl, bicycloalkyl, alkenyl, cycloalkenyl, or unsubstituted phenyl or phenyl bearing one or more alkyl, alkoxy, alkylthio, nitro, haloalkyl, haloalkoxy, cyano, halogen, carbalkoxy or hydroxy substituents, or unsubstituted pyridyl or pyridyl substituted in the same way, or $R^2$ and $R^3$ together denote unsubstituted or substituted polymethylene which may contain hetero atoms $R^4$ denotes halogen, cyano or the radicals

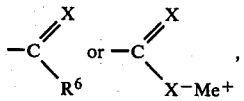

$R^6$ denoting unsubstituted or halogen-, alkoxy- or alkylthio-substituted methoxy, propoxy or isopropoxy, or lower unsubstituted or halogen-, alkoxy- or alkylthio-substituted alkyl, or alkylthio, amino, alkylamino or dialkylamino, X denotes oxygen or sulfur, and Me+ denotes an equivalent of a cation of the metals Li, Na, K, Mg, Ca, Ba, Al, Fe, Co, Ni, Mn, Cu and Zn, and $R^5$ denotes hydrogen or unsubstituted or halogen-, alkylthio-, alkoxy- or alkoxycarbonyl-substituted alkyl, or halogen, alkoxy, hydroxy, alkoxycarbonyl or unsubstituted phenyl or phenyl bearing one or more alkyl, alkoxy, alkylthio, nitro, haloalkyl, cyano, halogen, carbalkoxy or hydroxy substituents, and furthermore, $R^6$ denotes ethoxy, in which case $R^1$ does not simultaneously denote hydrogen, $R^5$ does not simultaneously denote methyl, $R^2$ does not simultaneously denote hydrogen, and $R^3$ does not simultaneously denote methyl, ethyl or unsubstituted phenyl or phenyl bearing methyl, chlorine or trifluoromethyl in 2-and/or 3-position or $R^1$ does not simultaneously denote hydrogen, $R^5$ does not simultaneously denote methyl, $R^2$ does not simultaneously denote methyl and $R^3$ does not simultaneously denote methyl, and $R^6$ also denotes hydroxy, in which case $R^1$ does not simultaneously denote hydrogen, $R^2$ does not simultaneously denote hydrogen, $R^3$ does not simultaneously denote unsubstituted phenyl or phenyl bearing methyl or trifluoromethyl in 2- and/or 3-position and $R^5$ does not simultaneously denote methyl, and the salts and metal complex compounds thereof, exhibit a good herbicidal action and a selective herbicidal action as regards crop plants and may be used as desiccants in various plants.

The new substituted 3-aminopyrazoles may be in the form of their salts with conventional strong inorganic or organic acids, such as hydrochloric acid, hydrobromic acid, nitric acid, sulfuric acid, tetrafluoboric acid, fluosulfonic acid, formic acid, a halogenated carboxylic acid, e.g. trichloroacetic acid, an alkanesulfonic acid, e.g. methanesulfonic acid, a halogenated alkanesulfonic acid, e.g. trifluomethanesulfonic acid, perfluohexanesulfonic acid, and an arylsulfonic acid, e.g. dodecylbenzenesulfonic acid.

On account of the tautomeric structure, two isomers occur in the starting materials of the new substituted 3-aminopyrazoles:

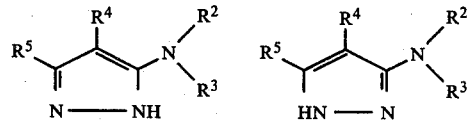

The isomer ratio is determined substantially by the various substituents. Therefore any formula or name may be understood to be either of the two isomers.

The new substituted 3-aminopyrazoles may be in the form of their metal complex compounds with transition metals, for example copper, iron, zinc, manganese, cobalt and nickel.

$R^1$ may for example denote the following:
hydrogen, methyl, ethyl, n-propyl, isopropyl, isobutyl, sec-butyl and tert-butyl, formyl, acetyl, propionyl, chloroacetyl, bromoacetyl, trichloroacetyl, trifluoroacetyl, 2,4-dichlorophenoxyacetyl, (2,4-chlorophenoxy)-propionyl, cyano, methoxycarbonyl, ethoxycarbonyl, isopropoxycarbonyl, phenoxycarbonyl, methylaminocarbonyl, isopropylaminocarbonyl, benzoyl, 2',4'-dichlorobenzoyl, methylsulfonyl, ethylsulfonyl, isopropylsulfonyl, phenylsulfonyl, 4-methylphenylsulfonyl, methylaminosulfonyl, isopropylaminosulfonyl, 3-chlorophenoxycarbonyl, 3,4-dichlorophenoxycarbonyl, 3-(methoxycarbonylamino)-phenoxycarbonyl, 2-methyl-4-chlorophenoxycarbonyl, methylaminothiocarbonyl, dimethylamino-(thio)-carbonyl, phenylamino-(thio)-carbonyl, and 3,4-dichlorophenylamino-(thio)-carbonyl.

R² may for example denote the following:
hydrogen, methyl, ethyl, n-propyl; isopropyl, 1-methoxy-2-propyl, formyl, acetyl and chloroacetyl.

R³ may for example denote the following:
methyl, ethyl, n-propyl, isopropyl, n-butyl, sec-butyl, isobutyl, tert-butyl, 3-methyl-2-butyl, pentyl-2, pentyl-3, hexyl-2, hexyl-3, 2-methyl-pentyl-3, 2,4-dimethylpentyl-3, 2-ethylhexyl, dodecyl, 1-methoxy-2-propyl, 1-fluoro-2-propyl, 1-chloro-2-propyl, 1,1,1-trifluoro-2-propyl, 1-cyano-2-propyl, 1-methoxycarbonyl-2-propyl, 2-(methoxycarbonyl)-2-propyl, benzyl, α-phenylethyl, β-phenylethyl, 2-(pyrazolyl-1)-ethyl, 2-(imidazolyl-1)-ethyl, 2-(1',2',4'-triazolyl)-ethyl, allyl, buten-1-yl-3, butyn-1-yl-3, 3-methyl-buten-1-yl-3, 3-methyl-butyn-1-yl-3, cyclopentyl, cyclohexyl, cycloheptyl, cyclooctyl, 2-methylcyclohexyl, 2-methoxycyclohexyl, 3-trifluoromethylcyclohexyl, 1,1-dimethoxypropyl-2, phenyl, 2-methylphenyl, 2-fluorophenyl, 3-chloro-4-fluorophenyl, 2,4-dichlorophenyl, 3,5-dichlorophenyl, 3-methoxyphenyl, 2,5-dimethoxyphenyl, 2-cyanophenyl, 2-nitrophenyl, 3-nitrophenyl, 2-methylthiophenyl, 2-trifluoromethylphenyl, 3-trifluoromethylphenyl, 2-methoxycarbonylphenyl, 3-methoxycarbonylphenyl, 2-hydroxyphenyl, 3-hydroxyphenyl, pyridyl-2, pyridyl-3, pyridyl-4,3-fluorophenyl, 2-chlorophenyl, 3,4-difluorophenyl, 2,4-difluorophenyl, 2,5-difluorophenyl, 2,3-dichlorophenyl, 2,5-dichlorophenyl, 2-methyl-3-chlorophenyl, 2-methyl-5-chlorophenyl, 2-methoxy-5-chlorophenyl, 3-tetrafluoroethoxyphenyl, 2-chloro-5-trifluoromethylphenyl, and 2-methoxy-5-methylphenyl.

R⁴ may for example denote the following:
chloro, bromo, cyano, methoxycarbonyl, ethoxycarbonyl, isopropoxycarbonyl, methoxythiocarbonyl, thiomethylcarbonyl, methylthiocarbonyl, acetyl, chloroacetyl, dichloroacetyl, trichloroacetyl, trifluoroacetyl, methoxyacetyl, amino, methylamino, dimethylamino, carboxyl, Na carboxylate, magnesium carboxylate, and manganese carboxylate.

R⁵ may for example denote the following:
hydrogen, methyl, isopropyl, tert-butyl, chloromethyl, methoxymethyl, cyanomethyl, methoxycarbonylmethyl, chloro, bromo, cyano, methoxy, isopropoxy, hydroxy, phenyl, 2-chlorophenyl, 2-methylphenyl, 3-methoxyphenyl, 3-methylthiophenyl, 4-nitrophenyl, 3-trifluoromethylphenyl, 2,4-dichlorophenyl, 3-cyanophenyl, 2-methoxycarbonylphenyl, and 2-hydroxyphenyl.

If R² and R³ together form polymethylene, the latter may contain hetero atoms, e.g. nitrogen, oxygen and sulfur. Together with the nitrogen atom in 3-position of the pyrazole, the following rings are formed for example:

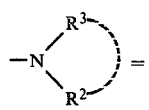

tetramethyleneimino, pentamethylenimino, hexamethylenimino, morpholino, thiomorpholino, and piperazino.

The ring formed together with R² and R³ may contain additional substituents such as alkyl, alkoxy, halogen and cyano.

Processes for the production of the new pyrazole derivatives are described for example in Chem. Ber. 98, 259 (1965).

Another method consists in condensing aldehydes, ketones or α-ketocarboxylic acid derivatives with 3-amino-4-alkoxycarbonyl pyrazoles which may be unsubstituted or substituted in 5-position, and subsequently hydrogenating the Schiff bases thus obtained.

The pyrazoles acylated in 1- or 2-position are obtained by subsequent acylation of the 3-aminopyrazole derivatives by conventional methods.

The salts of the new pyrazoles are prepared by reacting the pyrazoles with the acids in a solvent. The metal complex compounds of the new pyrazoles are prepared by reacting the pyrazoles with the metal salts in a solvent.

The processes selected for preparing the new pyrazoles are illustrated by the following Examples.

EXAMPLE 1

3-anilino-4-isopropoxycarbonyl-5-methylpyrazole 35.7 g of isopropyl 2-chloroacetate is added to a suspension of 33.5 g of 4-phenylthiosemicarbazide in 150 ml of tetrahydrofuran. After the mixture has been stirred for 30 minutes it is boiled for a further 30 minutes and then allowed to cool. The precipitated solid is isolated by suction filtering, washed with acetone and the residue is heated in a water/acetone mixture (1:1). After the separated sulfur has been poured off, the whole is allowed to cool and is neutralized with aqueous NaHCO₃, solution and the precipated solid is isolated; m.p. 138°–139° C. (from toluene).

EXAMPLE 2

2-isobutylamino-4-methoxycarbonyl-5-methylpyrazole 15.1 g of methyl 2-chloroacetate is added to a suspension of 14.7 g of 4-isobutylthiosemicarbazide in 150 ml of tetrahydrofuran. The mixture is stirred for 30 minutes and then boiled. After stirring for a further hour at 65° C., the mixture is cooled, the precipitated solid is isolated and washed with acetone. The residue is dissolved hot in water, filtered off from the precipitated sulfur and, after cooling, aqueous ammonia solution is added. After suction filtering and drying the product, 3-isobutylamino-4-methoxycarbonyl-5-methylpyrazole is isolated; m.p. 100°–103° C.

EXAMPLE 3

3-piperidino-4-methoxycarbonyl-5-methylpyrazole 4,4-pentamethylenethiosemicarbazide (m.p. 98°–99° C.) was prepared by the method disclosed in J. pr. Ch. (2) 159, 189 (1941). 32 g of 4,4-pentamethylenethiosemicarbazide is added to 100 ml of tetrahydrofuran (THF) and the whole is mixed with 31 g of methyl 2-chloroacetate. After stirring for one hour at room temperature, the solid formed is suction filtered, washed with acetone and dissolved in H₂O, and aqueous ammonia solution is added until the alkaline reaction (pH 8). The oil which separates is separated from the sulfur by extraction with CH₂Cl₂. After being concentrated it is recrystallized from acetone; m.p. 101°–102° C.

EXAMPLE 4

3-anilino-4-acetyl-5-methylpyrazole 50 g of 4-phenylthiosemicarbazide is suspended in 300 ml of tetrahydrofuran and 0.5 ml of concentrated HCl is added. Then 40.4 g of 3-chloroacetyl acetone is allowed to run in all at once and the whole is cooled with an ice-bath. After 12 hours' stirring, the precipitate formed is suction filtered, washed with acetone and then boiled in a water/acetone mixture (1:1). This hot solution is filtered off from the sulfur and neutralized with aqueous ammonia solution. The product is then suction filtered and recrystallized from acetone; m.p. 246°–247° C.

EXAMPLE 5

3-benzylamino-4-ethoxycarbonylpyrazole 21.2 g of benzaldehyde is added to a suspension of 25 g of 3-amino-4-ethoxycarbonylpyrazole in 200 ml of toluene. The whole is boiled while separating water. In 3 hours a total of 5 ml of water collects. After the toluene has been evaporated, 50 ml of methanol and 50 ml of THF are added and, under cooling, 23 g of $NaBH_4$ is added at 0°–5° C. After 4 hours' at room temperature, the solvent mixture is drawn off; then 200 ml of ice water is added the whole is extracted three times with 150 ml of methylene chloride each time and the extract is dried over $Na_2SO_4$. After concentration, an oil remains that is recrystallized from ligroin/toluene; m.p. 99°–100° C.

EXAMPLE 6

2,5-dimethyl-3-anilino-4-methoxycarbonylpyrazole 36.2 g of 2-methyl-4-phenylthiosemicarbazide is dissolved in 200 ml of methanol and 30.2 g of methyl 2-chloroacetate is added. After one hour's stirring, 10 ml of concentrated HCl is added, and the whole is then boiled. After the sulfur has separated, the mixture is allowed to cool, the sulfur is removed and the residue is evaporated.

The crystalline residue is neutralized with aqueous ammonia solution, separated and, after drying, recrystallized from hexane; m.p. 83°–86° C.

The compound 2,5-dimethyl-3-cyclohexylamino-4-methoxycarbonylpyrazole may be prepared analogously; b.p. (0.5 mm Hg) 113°–117° C.

EXAMPLE 7

2-phenyl-3-anilino-4-carboxymethyl-5-methylpyrazole

The same method was used as in Example 6 except that 2,4-diphenylthiosemicarbazide was used and THF as solvent; m.p. 111°–113° C.

The following tables contain some of the compounds that have been obtained according to a process of Examples 1–7.

TABLE 1

| No. | $R^2$ | $R^3$ | $R^5$ | $R^6$ | m.p. (°C.) |
|---|---|---|---|---|---|
| 1 | H | phenyl | tert.-butyl | $OC_2H_5$ | 108–110 |
| 2 | H | phenyl | phenyl | " | 143–145 |
| 3 | H | phenyl | 4-nitrophenyl | " | 154 |
| 4 | H | sec.-butyl | methyl | " | |
| 5 | H | tert.-butyl | methyl | " | |
| 6 | H | phenyl | hydrogen | " | |
| 7 | H | methyl | phenyl | " | |
| 8 | H | methyl | 4-chlorophenyl | " | |
| 9 | H | methyl | tert.-butyl | " | |
| 10 | H | phenyl | hydrogen | $OCH_3$ | 123–124 |
| 11 | H | cyclohexyl | hydrogen | " | |
| 12 | H | tert.-butyl | hydrogen | " | |
| 13 | H | sec.-butyl | hydrogen | " | |
| 14 | H | phenyl | methyl | " | 183–185 |
| 15 | H | 2-methylphenyl | methyl | " | 175–177 |
| 16 | H | 3-methylphenyl | methyl | " | 188–190 |
| 17 | H | 4-methylphenyl | methyl | " | 178–179 |
| 18 | H | 2-ethylphenyl | methyl | " | 166–167 |
| 19 | H | 2,6-dimethyl-phenyl | methyl | " | 190 |
| 20 | H | 2-methoxy-phenyl | methyl | " | 194 |
| 21 | H | 3-methoxy-phenyl | methyl | " | 173 |
| 22 | H | 4-methoxy-phenyl | methyl | " | 168–170 |
| 23 | H | 2-hydroxy-phenyl | methyl | " | |
| 24 | H | 3-hydroxy-phenyl | methyl | " | |
| 25 | H | 4-hydroxy-phenyl | methyl | " | |
| 26 | H | 2-chlorophenyl | methyl | " | |
| 27 | H | 3-chlorophenyl | methyl | " | 206–207 |
| 28 | H | 4-chlorophenyl | methyl | " | 201–202 |
| 29 | H | 2-fluorophenyl | methyl | " | 190–191 |
| 30 | H | 3-fluorophenyl | methyl | " | 182–184 |
| 31 | H | 4-fluorophenyl | methyl | " | 186–187 |
| 32 | H | 2-trifluoro- | methyl | " | 182–183 |

TABLE 1-continued

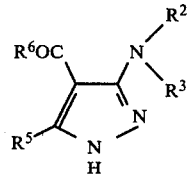

| | | | | | |
|---|---|---|---|---|---|
| 33 | H | 3-trifluoro-methylphenyl | methyl | " | 198 |
| 34 | H | 2,5-dimethyl-phenyl | methyl | " | 233–235 |
| 35 | H | 3,5-dimethyl-phenyl | methyl | " | 190–193 |
| 36 | H | 2,4-dichloro-phenyl | methyl | " | 207–210 |
| 37 | H | 3,4-dichloro-phenyl | methyl | " | 234–236 |
| 38 | H | 2,5-dichloro-phenyl | methyl | " | 251–253 |
| 39 | H | 3,5-dichloro-phenyl | methyl | " | |
| 40 | H | 3-chloro-4-fluorophenyl | methyl | " | 212 |
| 41 | H | 3,4-difluoro-phenyl | methyl | " | 204 |
| 42 | H | 2-methyl-3-chlorophenyl | methyl | " | 224–226 |
| 43 | H | 2-methyl-4-chlorophenyl | methyl | " | 205–206 |
| 44 | H | 2-methyl-5-chlorophenyl | methyl | " | more than 240 |
| 45 | H | 2-nitrophenyl | methyl | " | |
| 46 | H | 3-cyanophenyl | methyl | " | |
| 47 | H | 2-hydroxymethyl-phenyl | methyl | " | |
| 48 | H | 2-methylthio-phenyl | methyl | " | |
| 49 | H | 2-methoxycar-bonylphenyl | methyl | " | |
| 50 | H | 2-azaphenyl | methyl | " | |
| 51 | H | 3-azaphenyl | methyl | " | |
| 52 | H | 4-azaphenyl | methyl | " | |
| 53 | H | 2-methyl-3-aza-phenyl | methyl | " | |
| 54 | H | 2-methyl-6-aza-phenyl | methyl | " | |
| 55 | H | methyl | methyl | " | 155–157 |
| 56 | H | ethyl | methyl | " | 143–144 |
| 57 | H | n-propyl | methyl | | |
| 58 | H | allyl | methyl | " | 128–130 |
| 59 | H | isopropyl | methyl | " | 100–103 |
| 60 | H | 2-methylpropen-1-yl-3 | methyl | " | |
| 61 | H | 3-methylpropen-1-yl-3 | methyl | " | |
| 62 | H | propargyl | methyl | " | |
| 63 | H | 3-methylpropyn-1-yl-3 | methyl | " | |
| 64 | H | 3,3-dimethyl-propyn-1-yl-3 | methyl | " | |
| 65 | H | 3,3-dimethyl-propen-1-yl-3 | methyl | " | |
| 66 | H | n-butyl | methyl | " | 117–118 |
| 67 | H | iso-butyl | methyl | " | 100–103 |
| 68 | H | sec-butyl | methyl | " | 81–83 |
| 69 | H | tert-butyl | methyl | " | 115 |
| 70 | H | pentyl-2 | methyl | " | oil |
| 71 | H | pentyl-3 | methyl | " | 81–82 |
| 72 | H | 1-methyoxy-propyl-2 | methyl | " | $n_D^{21} = 1,5122$ |
| 73 | H | 1,1-dimethoxy-propyl-2 | methyl | " | |
| 74 | H | 1-methoxycar-bonyl-propyl-2 | methyl | " | |
| 75 | H | 1-ethoxycar-bonyl-propyl-2 | methyl | " | |
| 76 | H | 1-cyano-propyl-2 | methyl | " | |
| 77 | H | 1-methoxy- | methyl | " | oil |

TABLE 1-continued

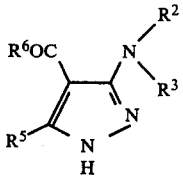

| No. | R² | R³ | R⁵ | R⁶ | m.p. (°C.) |
|---|---|---|---|---|---|
| | | butyl-2 | | | |
| 78 | H | 3-methoxy-propyl-1 | methyl | " | 107–108 |
| 79 | H | 1,3-dimethoxy-propyl-2 | methyl | " | |
| 80 | H | cyclopentyl | methyl | " | 83–85 |
| 81 | H | 2-methylcyclo-pentyl-1 | methyl | " | |
| 82 | H | cyclohexyl | methyl | " | 90–92 |
| 83 | H | 2-methylcyclo-hexyl | methyl | " | |
| 84 | H | 3-methylcyclo-hexyl | methyl | " | |
| 85 | H | 3-trifluoro-methylcyclohexyl | methyl | " | |
| 86 | H | cyclohexylmethyl | methyl | " | 138–140 |
| 87 | H | benzyl | methyl | " | 160–161 |
| 88 | H | 2-phenylethyl | methyl | " | 181–182 |
| 89 | H | bicyclo[2.2.1]-heptyl-2 (= norbonyl) | methyl | " | 127–130 |
| 90 | H | adamantyl | methyl | " | 202–203 |
| 91 | H | cycloheptyl | methyl | " | |
| 92 | H | cyclooctyl | methyl | " | 145–147 |
| 93 | H | phenyl | ethyl | " | |
| 94 | H | phenyl | isopropyl | " | 103–104 |
| 95 | H | phenyl | tert-butyl | " | |
| 96 | H | methyl | tert-butyl | " | |
| 97 | H | methyl | phenyl | " | 168–169 |
| 98 | methyl | methyl | methyl | " | 118–119 |
| 99 | methyl | ethyl | methyl | " | oil |
| 100 | methyl | isopropyl | methyl | " | 96–98 |
| 101 | methyl | sec-butyl | methyl | " | oil |
| 102 | methyl | 1-methoxy-2-propyl | methyl | " | |
| 103 | methyl | 1-methoxy-2-butyl | methyl | " | |
| 104 | methyl | tert-butyl | methyl | " | |
| 105 | methyl | cyclohexyl | methyl | " | 118–119 |
| 106 | methyl | phenyl | methyl | " | oil |
| 107 | ethyl | ethyl | methyl | " | 90–92 |
| 108 | ethyl | cyclohexyl | methyl | " | 109–110 |
| 109 | ethyl | phenyl | methyl | " | oil |
| 110 | 1-methoxy-2-propyl | phenyl | methyl | " | |
| 111 | iso-propyl | phenyl | methyl | " | 91–92 |

| No. | R² + R³ | R⁵ | R⁶ | m.p. (°C.) |
|---|---|---|---|---|
| 112 | tetramethylene | methyl | OCH₃ | 133–134 |
| 113 | pentamethylene | methyl | " | 101–102 |
| 114 | hexamethylene | methyl | " | oil |
| 115 | 3-oxapentamethylene | methyl | " | 89–90 |
| 116 | 3-iminopentamethylene | methyl | " | |

| No. | R² | R³ | R⁵ | R⁶ | m.p. (°C.) |
|---|---|---|---|---|---|
| 117 | methyl | n-butyl | methyl | OCH₃ | oil |
| 118 | methyl | isobutyl | methyl | " | oil |
| 119 | H | 2-methoxy-5-nitrophenyl | methyl | " | |
| 120 | 1-methoxy-2-propyl | 2-methyl-phenyl | methyl | " | |
| 121 | 1-methoxy-2-propyl | 4-methyl-phenyl | methyl | " | |
| 122 | methyl | 3-methoxy-phenyl | methyl | " | oil |
| 123 | H | phenyl | methyl | methyl | 247 |
| 124 | H | phenyl | hydrogen | methyl | |
| 125 | H | phenyl | trifluoromethyl | methyl | |
| 126 | H | 2-methoxy-5-chlorophenyl | methyl | OCH₃ | 253–254 |
| 127 | H | sec-butyl | methyl | methyl | |

TABLE 1-continued

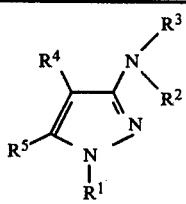

| No. | | R² | R³ | | m.p. (°C.) |
|---|---|---|---|---|---|
| 128 | H | tert-butyl | methyl | methyl | |
| 129 | H | tert-butyl | methyl | trifluoromethyl | |
| 130 | H | tert-butyl | trifluoromethyl | methyl | |
| 131 | H | cyclohexyl | methyl | methyl | more than 250 |
| 132 | H | 2-fluorophenyl | methyl | methyl | 250–252 |
| 133 | H | 2-fluorophenyl | methyl | methyl | |
| 134 | H | 2-azaphenyl | methyl | methyl | |
| 135 | H | 3-azaphenyl | methyl | methyl | |
| 136 | H | phenyl | methyl | amino | more than 250 |
| 137 | H | phenyl | methyl | methylamino | |
| 138 | H | phenyl | methyl | dimethylamino | |
| 139 | H | tert-butyl | methyl | amino | |
| 140 | H | sec-butyl | methyl | methylamino | |

EXAMPLE 8

1-acetyl-3-anilino-4-methoxycarbonyl-5-methylpyrazole 23 g of 3-anilino-4-methoxycarbonyl-5-methylpyrazole is dissolved in 51 g of acetic anhydride and brought to the boil. After 15 minutes' boiling the mixture is allowed to cool, poured into ice water and stirred for 30 minutes. The solid which separates is isolated and recrystallized from methanol; m.p. 115°–116° C.

The position of the acetyl group was determined by means of the IR spectrum (CO band at 1720 cm$^{-1}$).

This result merely rules out that the anilino radical was acetylated. X-ray structural analysis has shown that the acetyl radical is in 1-position of the pyrazole ring.

EXAMPLE 9

1-acetyl-3-cyclohexylamino-4-methoxycarbonyl-5-methylpyrazole

This compound is prepared in a manner analogous to that described in Example 6, except that the starting materials are reacted at room temperature with cooling. The reaction lasts 1 hour; m.p. 140°–142° C.

Further derivatives of pyrazoles which have been obtained by one of the methods of the Examples or other prior art methods are listed in the following Table.

| No. | R¹ | R² | R³ | R⁴ | R⁵ | m.p. (°C.) |
|---|---|---|---|---|---|---|
| 141 | formyl | hydrogen | phenyl | —CO₂CH₃ | methyl | |
| 142 | formyl | " | sec-butyl | " | " | |
| 143 | formyl | " | tert-butyl | " | " | |
| 144 | acetyl | " | phenyl | " | " | 116 |
| 145 | chloroacetyl | " | phenyl | " | " | 145–147 |
| 146 | methylsulfonyl | " | " | " | " | 201–203 |
| 147 | methylaminocarbonyl | " | " | " | " | 127 |
| 148 | trifluoroacetyl | " | " | " | " | |
| 149 | propionyl | " | " | " | " | 120–122 |
| 150 | benzoyl | " | " | " | " | 155–156 |
| 151 | methoxy- | " | " | " | " | 142 |

-continued

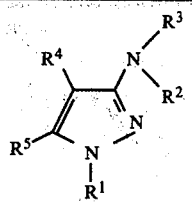

| No. | R¹ | R² | R³ | R⁴ | R⁵ | m.p. (°C.) |
|---|---|---|---|---|---|---|
| 152 | ethoxycarbonyl | " | " | " | " | 130–132 |
| 153 | acetyl | " | 2-methylphenyl | " | " | 145–147 |
| 154 | acetyl | " | 3-methylphenyl | " | " | 86–89 |
| 155 | acetyl | " | 2-fluorophenyl | " | " | 144–146 |
| 156 | acetyl | " | 3-fluorophenyl | " | " | 135–136 |
| 157 | acetyl | " | 4-fluorophenyl | " | " | 132–134 |
| 158 | acetyl | " | sec-butyl | " | " | 76–77 |
| 159 | acetyl | " | tert-butyl | " | " | 120 |
| 160 | acetyl | " | cyclopentyl | " | " | 96–98 |
| 161 | acetyl | " | cyclohexyl | " | " | 140–142 |
| 162 | acetyl | " | norbonyl | " | " | 139–142 |
| 163 | acetyl | acetyl | cyclohexyl | " | " | 110–112 |
| 164 | acetyl | methyl | cyclohexyl | " | " | 80–82 |
| 165 | acetyl | " | phenyl | " | " | 88–90 |
| 166 | " | hydrogen | tert-butyl | acetyl | " | 146 |
| 167 | " | methyl | " | " | " | |
| 168 | " | hydrogen | phenyl | " | " | 140–142 |
| 169 | " | methyl | " | " | " | |
| 170 | " | hydrogen | 2-fluorophenyl | " | " | |
| 171 | " | " | cyclohexyl | " | " | |
| 172 | " | " | tert-butyl | trifluoroacetyl | " | |
| 173 | trifluoroacetyl | " | " | trifluoroacetyl | " | |
| 174 | methoxycarbonyl | " | phenyl | acetyl | " | |
| 175 | methoxycarbonyl | " | tert-butyl | methoxycarbonyl | " | |
| 176 | ethoxycarbonyl | " | " | methoxycarbonyl | " | |
| 177 | methoxycarbonyl | " | " | acetyl | " | |
| 178 | cyano | " | phenyl | " | " | |
| 179 | " | " | " | methoxycarbonyl | " | |
| 180 | acetyl | " | " | cyano | " | |
| 181 | " | methyl | ethyl | methoxycarbonyl | " | 41–41 |
| 182 | " | " | isopropyl | methoxycarbonyl | " | 75–76 |
| 183 | " | " | n-butyl | methoxycarbonyl | " | |
| 184 | " | " | iso-butyl | methoxycarbonyl | " | |
| 185 | " | " | sec-butyl | methoxycarbonyl | " | 51–53 |
| 186 | " | " | tert-butyl | methoxycarbonyl | " | |
| 187 | " | ethyl | phenyl | methoxycarbonyl | " | 71–72 |
| 188 | " | isopropyl | " | meth- | " | |

-continued

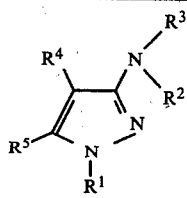

| No. | R¹ | R² | R³ | R⁴ | R⁵ | m.p. (°C.) |
|---|---|---|---|---|---|---|
| 189 | " | 1-methoxy-2-propyl | " | methoxycarbonyl | " | |
| 190 | " | 1-methoxy-2-propyl | 2-methylphenyl | methoxycarbonyl | " | |
| 191 | " | 1-methoxy-2-propyl | 4-methylphenyl | methoxycarbonyl | " | |
| 192 | " | 3-methoxyphenyl | methyl | methoxycarbonyl | " | |
| 193 | " | 4-methoxyhenyl | H | methoxycarbonyl | " | 126–128 |
| 194 | $-\overset{\underset{\parallel}{O}}{C}-CH_2Cl$ | H | C₄H₉sec | COOCH₃ | CH₃ | 63 |
| 195 | H | H | phenyl | $-\overset{\underset{\parallel}{O}}{C}-$phenyl | CH₃ | 196 |
| 196 | H | H | cyclohexyl | —COO—iPr | CH₃ | 105–107 |
| 197 | H | H | —CH₂—phenyl | —COOC₂H₅ | H | |
| 198 | H | H | —CH(CH₃)—iPr | —COOCH₃ | CH₃ | oil |
| 199 | H | H | 1-methoxypropyl | dimethylcarbamoyl | methyl | |
| 200 | H | H | 3-hydroxyphenyl | —CO₂C₂H₅ | " | 215–217 |
| 201 | H | H | phenyl | —CO₂CH₃ | phenyl | 139–140 |
| 202 | phenoxycarbonyl | H | " | " | methyl | 136–138 |
| 203 | acetyl | CH₃ | 1-methoxy-2-propyl | " | " | 52–53 |
| 204 | H | H | 3-fluorophenyl | " | H | 160 |
| 205 | H | H | 2-fluorophenyl | " | " | |
| 206 | H | H | 3-methoxyphenyl | " | " | |
| 207 | H | H | phenyl | " | methoxymethyl | 125–126 |
| 208 | H | H | phenyl | " | chloromethyl | 156–157 |
| 209 | H | H | phenyl | " | —CH₂—CO₂CH₃ | 156–157 |
| 210 | H | H | " | " | —CO₂CH₃ | |
| 211 | H | H | tert-butyl | " | Br | |
| 212 | H | H | 2,3-dichlorophenyl | " | CH₃ | 253–255 |
| 213 | H | H | 2,3-dimethylphenyl | " | " | 216–218 |
| 214 | H | H | 2-cyanophenyl | " | " | |
| 215 | H | H | 3-nitrophenyl | " | " | |
| 216 | H | H | 3-methoxycarbonylphenyl | " | " | |
| 217 | H | H | 2-chloro-5-trifluoromethylphenyl | " | " | more than 240 |
| 218 | H | H | 2,5-dimethoxyphenyl | " | " | 180–181 |
| 219 | H | H | 2-methoxy-5-methylphenyl | " | " | 192 |

-continued

| No. | R¹ | R² | R³ | R⁴ | R⁵ | m.p. (°C.) |
|---|---|---|---|---|---|---|
| 220 | acetyl | H | sec-butyl | COOCH₃ | H | 76–77 |
| 223 | " | H | phenyl | —CO₂C₃H₇ | —CH₃ | 121 |
| 224 | " | H | " | —CO₂CH₃ | CH₂—CO₂CH₃ | 142–143 |
| 225 | —CH—CO—N(CH₃)₂<br>\|<br>CH₃ | H | phenyl | " | CH₃ | 165–166 |
| 226 | H | H | phenyl | —CN | CH₃ | 221–222 |
| 227 | H | H | 3-methyl-4-fluorophenyl | —CO₂CH₃ | —CH₃ | 192–194 |
| 228 | acetyl | H | 3-methyl-4-fluorophenyl | " | " | 115 |
| 229 | acetyl | H | 2-methyl-4-fluorophenyl | " | " | 163–164 |
| 230 | H | H | 2-methyl-5-fluorophenyl | " | " | 230–232 |
| 231 | acetyl | H | 2-methyl-5-chlorophenyl | " | " | 191–192 |
| 232 | acetyl | H | 3,4-dichlorophenyl | " | " | 142–143 |
| 233 | acetyl | H | 4-methylphenyl | " | " | 130–132 |
| 234 | " | H | 4-chlorophenyl | " | " | 150–153 |
| 235 | " | H | α-phenylethyl | " | " | 92–93 |
| 236 | " | H |  | " | " | 135–136 |
| 237 | " | H | 2,5-dimethoxyphenyl | " | " | 177–178 |
| 238 | " | H | 2-methoxy-5-chlorophenyl | " | " | 221–223 |
| 239 | " | H | 2,3-dichlorophenyl | " | " | 124–125 |
| 240 | " | H | 2,5-dichlorophenyl | " | " | 180–182 |
| 241 | " | H | 2-trifluoromethylphenyl | " | " | 147–148 |
| 242 | H | H | 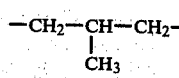 | " | " | 153 |
| 243 | H | n-C₃H₇ | n-C₃H₇ | " | " | 56–58 |
| 244 | H | H | —CH₂—CH—CH₂—⟨phenyl⟩—C(CH₃)₃<br>\|<br>CH₃ | " | " | oil |
| 245 | H | H | 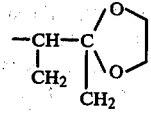 | " | " | amorphous glass |
| 246 | H | H | 2,4-difluorophenyl | " | " | 184–185 |
| 247 | H | H | 2,5-difluorophenyl | " | " | 222 |
| 248 | 2,4-dichlorophenoxyacetyl | H | phenyl | " | " | 197–198 |
| 249 | α-(2,4-dichlorophenoxy)propionyl | H | phenyl | " | " | 152–154 |
| 250 | H | CH₃ | 3-methoxyphenyl | " | " | oil |
| 251 | phenoxycarbonyl | H | pentyl-3- | " | " | 94–96 |
| 252 | dimethyl- | H | phenyl | " | " | 136 |

-continued

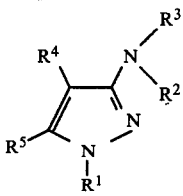

| No. | R¹ | R² | R³ | R⁴ | R⁵ | m.p. (°C.) |
|-----|-----|-----|-----|-----|-----|-----|
| 253 | carbonyl −C(=O)−O−(phenyl with NHCO₂CH₃) | H | " | " | " | 165–167 |
| 254 | −C(=O)−C(CH₃)(H)−CH₂O−C(=O)−CH₃ | H | H | phenyl | " | " | 102 |
| 255 | phenoxy-carbonyl | H | 3-methoxyphenyl | " | " | 165–166 |
| 256 | p-toluyl-sulfonyl | H | phenyl | " | " | |

EXAMPLE 10

The sulfur-containing hydrochloride obtained from 14.7 g of 4-tert-butylthiosemicarbazide and 15.1 g of methyl 2-chloroacetate in 200 ml of tetrahydrofuran is suspended in 100 ml of methanol and boiled. On cooling, the solution filtered hot separates the hydrochloride from 3-tert-butylamino-4-methoxycarbonyl-5-methylpyrazole. Colorless crystals, m.p. 178° C.

The following compounds were prepared analogously.

| No. | R¹ | R² | R³ | R⁴ | R⁵ | salt | m.p. (°C.) |
|-----|-----|-----|-----|-----|-----|-----|-----|
| 221 | H | CH₃ | C₂H₅ | COOCH₃ | CH₃ | hydrochloride | 147–149 |
| 222 | H | CH₃ | 2-n-butyl | COOCH₃ | CH₃ | hydrochloride | 173–175 |

Application may be effected for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure a fine distribution of the active ingredient.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethylsulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenol polyglycol ethers, alkylaryl polyester alcohols, isotridecyl alcohols, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90%, by weight of active ingredient.

The new compounds exhibit herbicidal action and are suitable for removing or suppressing unwanted plant growth in crops or on non-crop land. It is natural that individual active ingredients have varying intensities or differ in their effect on unwanted plants or crop plants. Their influence on unwanted plants is illustrated in the Tables below. The series of experiments were carried out in the greenhouse and in the open.

I. Greenhouse experiments

Plastic flowerpots having a volume of 300 cm$^3$ were filled with a loamy sand containing about 1.5% of humus. The seeds of the test plants according to Table 1, split up into species, were sown shallowly therein. Immediately afterwards, in the case of preemergence treatment, the active ingredients were applied to the surface of the soil. They were suspended or emulsified in water as distributing agent and sprayed onto the soil by means of atomizing nozzles. After the agents had been applied, the pots were lightly sprinkler-irrigated in order to stimulate germination and growth of the plants and at the same time activate the chemical agents. The pots were then covered with transparent plastic hoods until the plants had emerged. The covering effected uniform germination of the test plants, where this was not impaired by the chemicals, and prevented readily volatile active ingredients from evaporating.

For the purpose of the postemergence treatment, the plants were first grown to a height of 3 to 10 cm, depending on their habit, in the pots and then treated. They were not covered. The tests were carried out in a greenhouse, the warmer sections of the greenhouse (25° to 40° C.) being preferred for the warmth-loving species and 15° to 30° C. for those of temperature climates. The experimental period was from 4 to 6 weeks. During this period the plants were tended and their reactions to the various treatments were evaluated. The following tables contain the test substances, the various rates of application in kg/ha of active substance and the species of test plants. Assessment is on a scale of 0 to 100, 0 denoting no damage or normal emergence and 100 denoting no emergence of the plants or complete destruction at least of the parts of the shoots above the ground.

II. Experiments in the open

These were experiments on small plots at locations with loamy sand of pH 5–6 and a humus content of 1 to 1.5%. Postemergence treatments are described which have been carried out on young test plants in the early growth stages up to a height of 5 cm. The weed flora of the most varied species was governed by the time of year (e.g. spring-germinating species and summer-germinating species). The compounds were emulsified or suspended in water as carrier and distribution medium and applied with the aid of a motor-driven plot spray mounted on a hitch. When there was no natural precipitation, the plots were sprinkler-irrigated in order to ensure the germination and growth of the plants. All the experiments lasted several weeks. Then the evaluation was carried out using the scale 0 to 100.

Results

Tables 2 to 13 contain the results of the experiments.

It has become evident that the new 3-aminopyrazole derivatives have interesting herbicidal properties in pre- and postemergence application and differ from the comparative agents.

What is particularly striking is the broad spectrum of action, numerous unwanted broadleaved and grass plants being controlled. In this aspect, in particular, the new compounds offer substantial advantages over the prior art comparative active ingredients.

There are various ways of applying the compounds of the invention.

1. The agents may be used for the selective control of unwanted plants in various crops, including ornamental lawns, e.g. Bermudagrass (Table 6). The latter may be monocotyledonous or dicotyledonous herbaceous crop plants, the agents also coming into direct contact with the leaves or the leaves of the crop plants. However, application techniques may also be used in which spraying equipment is used that enables the agents to be sprayed in such a way that the leaves of sensitive crop plants are not touched if possible and the agents come into contact only with the soil beneath or the unwanted plants growing in it (post-directed or lay-by).

2. The broad spectrum of species from the most varied families that can be controlled also means that the agents are suitable for destroying unwanted broadleaves and grass weeds in woody trees and bushes as well as sugar cane.

3. Furthermore the agents can be used on non-crop areas such as industrial and railroad areas, parking and storage areas, paths, edges of ditches, and forest cutover land. Here it is more a question of the application rate whether the plants are completely eliminated or merely have their growth suppressed and retarded without the plants dying.

4. The compounds tested include those that are suitable for drying green leaves and stems (desiccants). Such agents are used for example for killing potato tops before the mechanical potato harvest, for controlling weeds that break through in ripe cereal fields before the harvest, for accelerating the drying of soya beans before combine harvesting, and for removing green vegetation in cotton which is ready for picking before the harvest.

In view of the variety of application methods the agents of the invention or compositions containing same may be used for removing unwanted plant growth in a large number of crop in addition to those listed in the Tables. The rates of application may vary from 0.1 to 15 kg/ha or more depending on the object to be controlled.

The following are examples of crop plants.

| Botanical name | English term |
|---|---|
| *Allium cepa* | onions |
| *Ananas comosus* | pineapple |
| *Arachis hypogaea* | peanuts (groundnuts) |
| *Asparagus officinalis* | asparagus |
| *Avena sativa* | oats |
| *Beta vulgaris* spp. *altissima* | sugar beets |
| *Beta vulgaris* spp. *rapa* | fodder beets |
| *Beta vulgaris* spp. *esculenta* | table beets, red beets |
| *Brassica napus* var. *napus* | rape |
| *Brassica napus* var. *napobrassica* | |
| *Brassica napus* var. *rapa* | turnips |
| *Brassica rapa* var. *silvestris* | |
| *Camellia sinensis* | tea plants |
| *Carthamus tinctorius* | safflower |
| *Citrus limon* | lemon |
| *Citrus maxima* | grapefruits |
| *Citrus reticulata* | |
| *Citrus sinensis* | orange trees |
| *Coffea arabica* (*Coffea canephora*, *Coffea liberica*) | coffee plants |
| *Cucumis melo* | melons |

| Botanical name | English term |
|---|---|
| Cucumis sativus | cucumber |
| Cynodon dactylon | Bermudagrass in turfs and lawns |
| Dauces carota | carrots |
| Elaeis guineensis | oil palms |
| Fragaria vesca | strawberries |
| Glycine max | soybeans |
| Gossypium hirsutum (Gossypium arboreum Gossypium herbaceum Gossypium vitifolium) | cotton |
| Helianthus annuus | sunflowers |
| Helianthus tuberosus | |
| Hevea brasiliensis | rubber plants |
| Hordeum vulgare | barley |
| Humulus lupulus | hop |
| Ipomoea batatas | sweet potato |
| Lactuca sativa | lettuce |
| Lens culinaris | lentils |
| Linum usitatissimum | flax |
| Lycopersicon lycopersicum | tomato |
| Malus spp. | apple trees |
| Manihot esculenta | cassava |
| Medicago sativa | alfalfa (lucerne) |
| Mentha piperita | peppermint |
| Musa spp. | banana plants |
| Nicotiana tabacum (N. rustica) | tobacco |
| Olea europaea | olive trees |
| Oryza sativa | rice |
| Panicum miliaceum | |
| Phaseolus lunatus | limabeans |
| Phaseolus mungo | mungbeans |
| Phaseolus vulgaris | snapbeans, green beans, dry beans |
| Pennisetum glaucum | |
| Petroselinum crispum spp. tuberosum | parsley |
| Picea abies | Norway spruce |
| Abies alba | fire |
| Pinus spp. | pine trees |
| Pisum sativum | English peas |
| Prunus avium | cherry trees |
| Prunus domestica | plum trees |
| Prunus persica | peach trees |
| Pyrus communis | pear trees |
| Ribes sylvestre | red currants |
| Ribes uva-crispa | |
| Ricinus communis | |
| Saccharum officinarum | sugar cane |
| Secale cereale | rye |
| Sesamum indicum | Sesame |
| Solanum tuberosum | Irish potatoes |
| Sorghum bicolor (s. vulgare) | grain sorghum |
| Sorghum dochna | |
| Spinacia oleracea | spinach |
| Theobrome cacao | cacao plants |
| Trifolium pratense | red clover |
| Triticum aestivum | wheat |
| Vaccinium corymbosum | blueberry |
| Vaccinium vitis-idaea | cranberry |
| Vicia faba | tick beans |
| Vigna sinensis (V. unguiculata) | cow peas |
| Vitis vinifera | grapes |
| Zea mays | Indian corn, sweet corn, maize |

To further increase the spectrum of action of the new individual active ingredients, to achieve synergistic effects or to improve persistence in the soil, numerous other herbicidal compounds and growth regulators may be used as components for mixtures and combination. Depending on the area of use and the unwanted plants to be controlled, the following substances or similar derivatives are suitable as components:

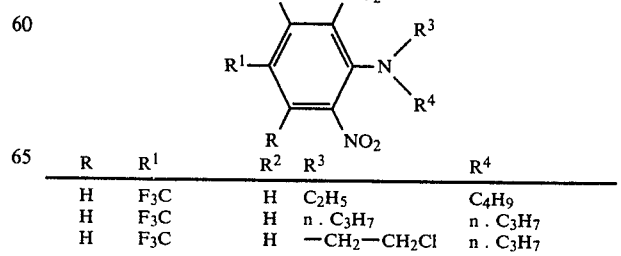

-continued

| | | | | |
|---|---|---|---|---|
| H | SO₂NH₂ | H | n.C₃H₇ | n.C₃H₇ |
| H | F₃C | H | nC₃H₇ | −CH₂−◁ |
| H₃C | H₃C | H | H | −CH(C₂H₅)CH(C₂H₅) — i.e. $-CH(C_2H_5)_2$ |

$$\underset{R}{\overset{R^1}{N}}-\overset{O}{\underset{\|}{C}}-O-R^2$$

| R | R¹ | R² |
|---|---|---|
| 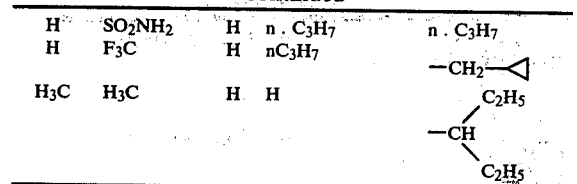 C₆H₅ / CH₃-substituted phenyl | H | iC₃H₇ |
| 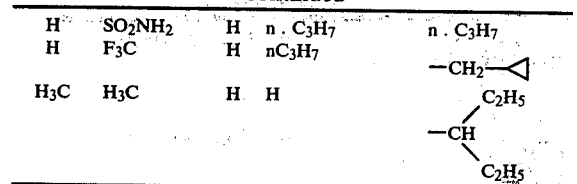 3-Cl-C₆H₄ | H | −CH₂−C₆H₃(Cl)(Cl) |
| 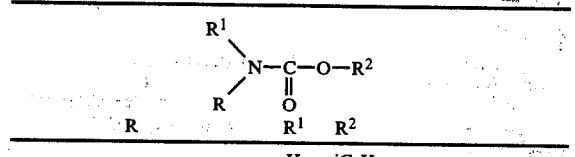 3-Cl-C₆H₄ | H | $-\underset{CH_3}{CH}-C\equiv CH$ |
| 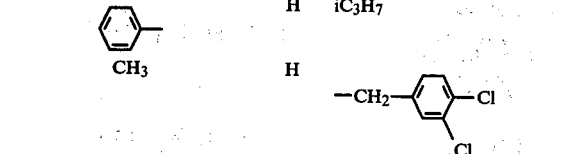 Cl-C₆H₄ | H | iC₃H₇ |
| 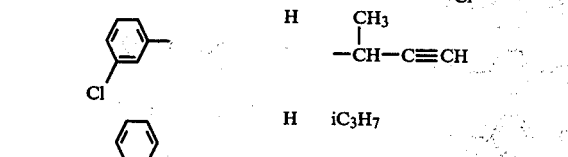 C₆H₅ | H | $-\underset{CH_3}{CH}-\underset{\|O}{\overset{\|}{C}}-NH-C_2H_5$ |
| H₂N−C₆H₄−SO₂− | H | CH₃ |

$$R-\underset{R^1}{N}-\overset{O}{\underset{\|}{C}}-O-\text{(phenyl)}-NH-\overset{O}{\underset{\|}{C}}-O-R^2$$

| R | R¹ | R² |
|---|---|---|
| 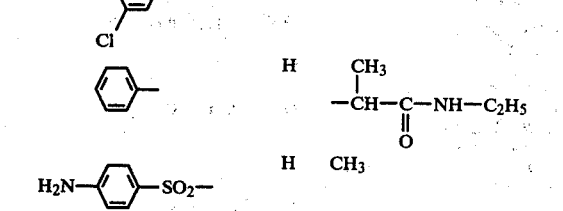 3-CH₃-C₆H₄ | H | CH₃ |
| 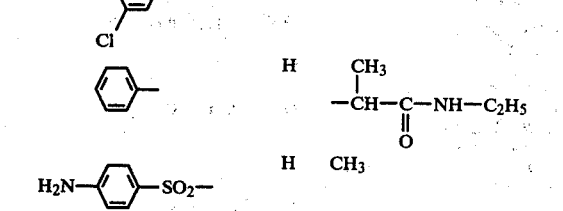 C₆H₅ | H | C₂H₅ |
| 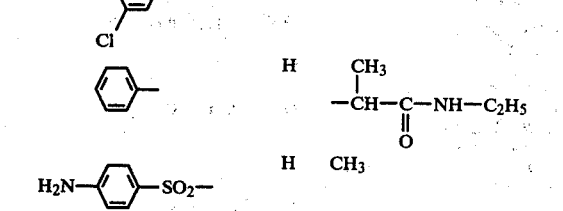 C₆H₅ | CH₃ | CH₃ |
| 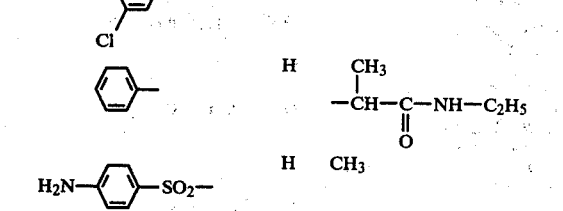 4-F-C₆H₄ | H | CH₃ |

$$\underset{R}{\overset{R^1}{N}}-\overset{O}{\underset{\|}{C}}-S-R^2$$

| R | R¹ | R² |
|---|---|---|
| iC₃H₇ | iC₃H₇ | CH₂−CCl=CCl₂ |
| iC₃H₇ | iC₃H₇ | CH₂−CCl=CHCl |
| n.C₃H₇ | n.C₃H₇ | C₂H₅ |

$$R-\underset{Y}{\overset{X}{C}}-\overset{O}{\underset{\|}{C}}-O-R^1$$

| R | X | Y | R¹ |
|---|---|---|---|
| CH₃ | Cl | Cl | Na |
| 2,4,5-Cl₃-C₆H₂−O−C₆H₄−O− | Cl | Cl | Na |
| 4-Cl-C₆H₄−O−C₆H₄−O− | H | CH₃ | CH₃ |
| 4-Cl-C₆H₄−O−C₆H₄−O− | H | CH₃ | −CH₂−CH(CH₃)₂ |
| 3,5-Cl₂-pyridin-2-yl−O−C₆H₄−O− | H | CH₃ | Na |
| 2-Cl-4-CF₃-C₆H₃−O−C₆H₄−O− | H | CH₃ | Na |

$$\underset{R}{\overset{R^1}{N}}-\overset{O}{\underset{\|}{C}}-R^2$$

| R | R¹ | R² |
|---|---|---|
| 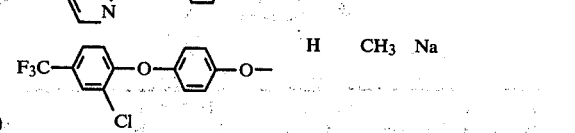 2,6-Cl₂-C₆H₃ | H | −◁ |
| 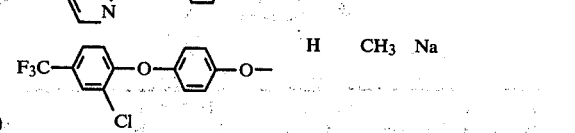 2,6-Cl₂-C₆H₃ | H | C₂H₅ |
| 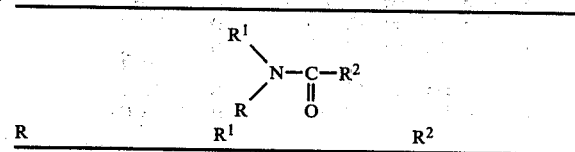 C₆H₅ | $-\underset{CH_3}{CH}-C\equiv CH$ | CH₂Cl |
| 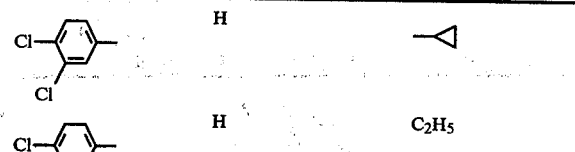 2-CH₃-6-C₂H₅-C₆H₃ | $-\underset{CH_3}{CH}-CH_2-OCH_3$ | CH₂Cl |
| 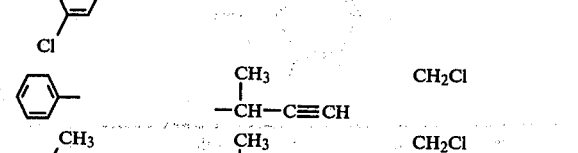 2,6-(C₂H₅)₂-C₆H₃ | −CH₂−OCH₃ | CH₂Cl |
| 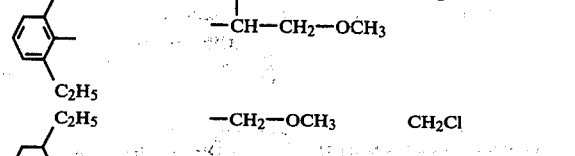 2,6-(C₂H₅)₂-C₆H₃ | $-CH_2-\overset{O}{\underset{\|}{C}}-OC_2H_5$ | CH₂Cl |
| 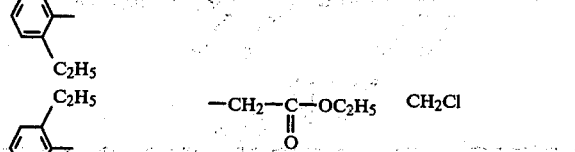 C₆H₅ | iC₃H₇ | CH₂Cl |
| 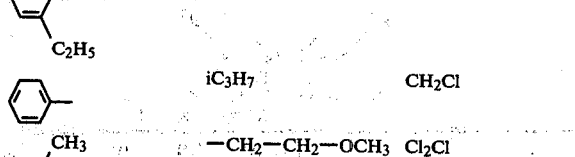 2,6-(CH₃)₂-C₆H₃ | −CH₂−CH₂−OCH₃ | Cl₂Cl |
| C₂H₅ | C₂H₅ | $-\underset{CH_3}{CH}-O-\text{(naphthyl)}$ |
| HC≡C−C(CH₃)₂− | H | 3,5-Cl₂-C₆H₃ |

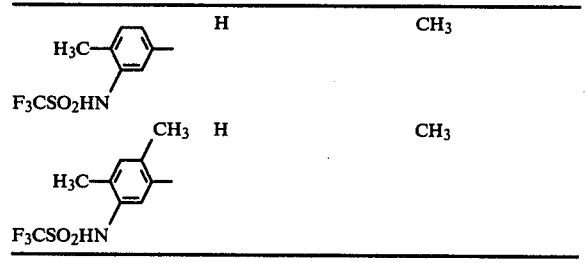
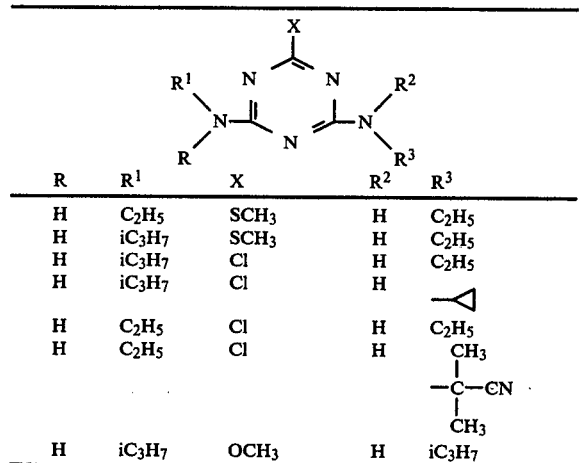
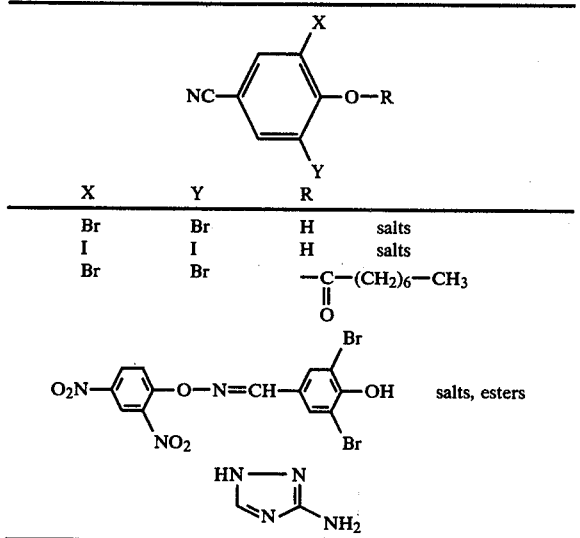
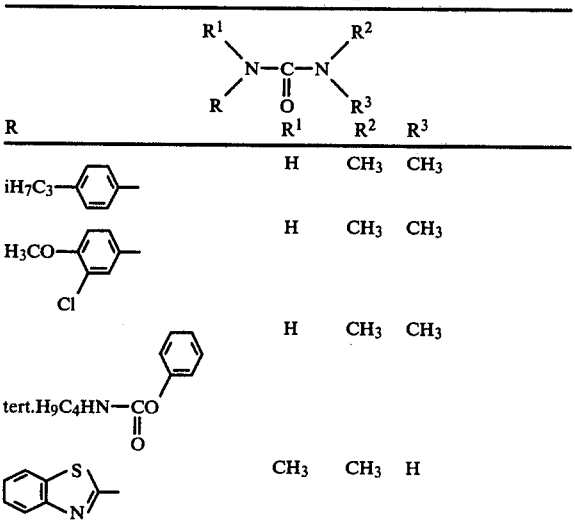
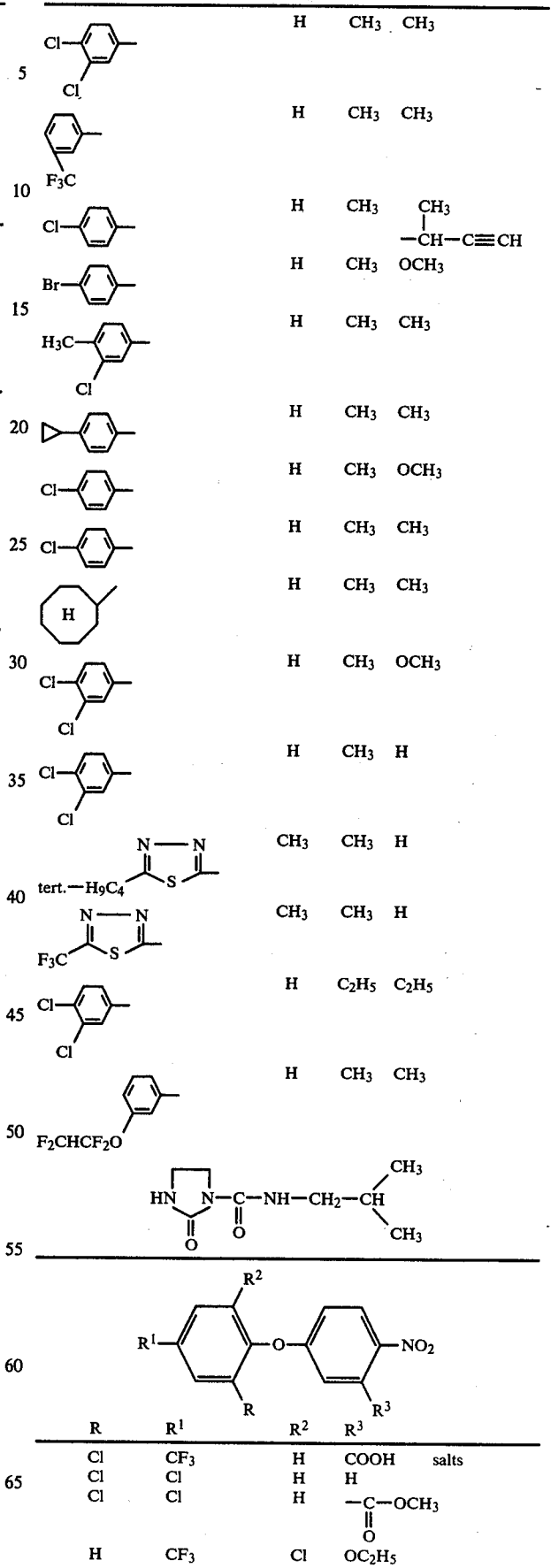

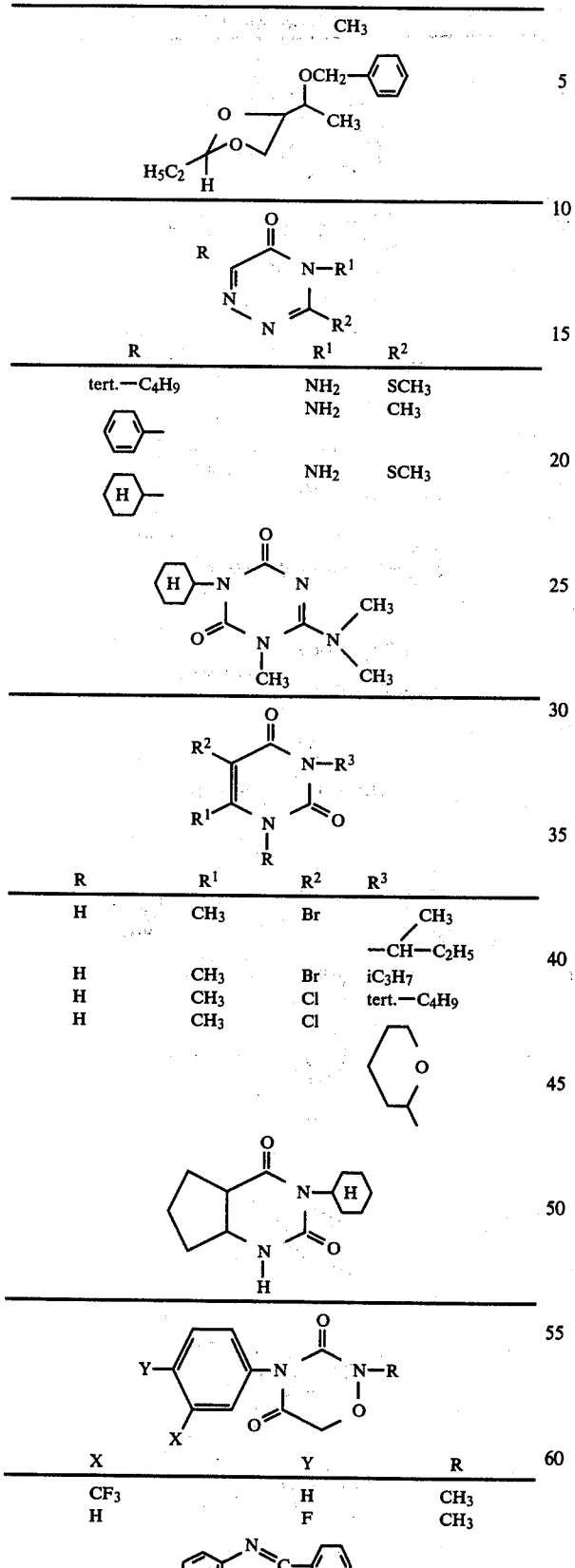
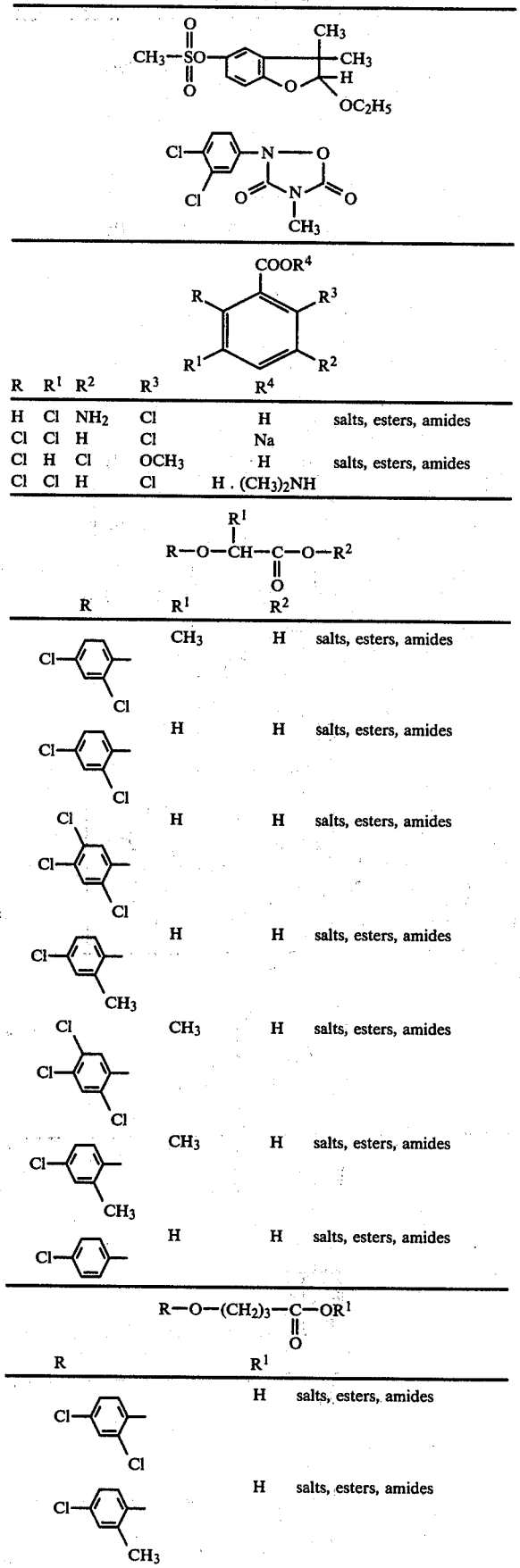

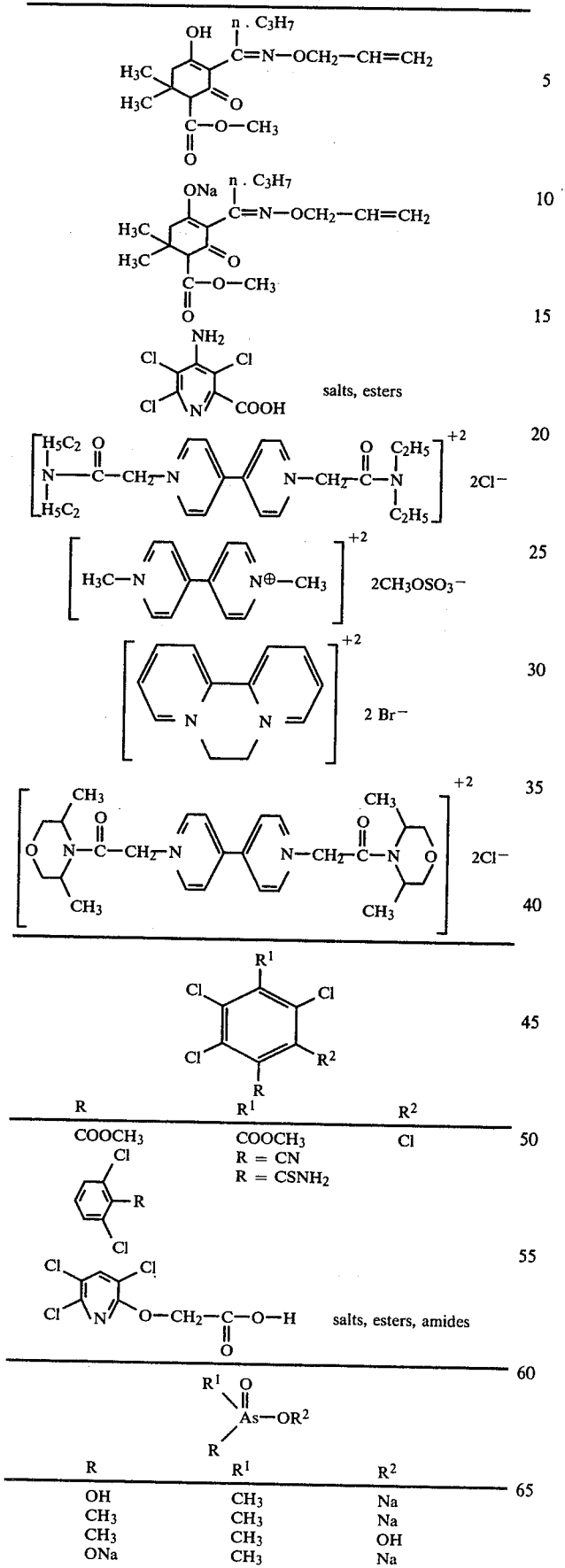
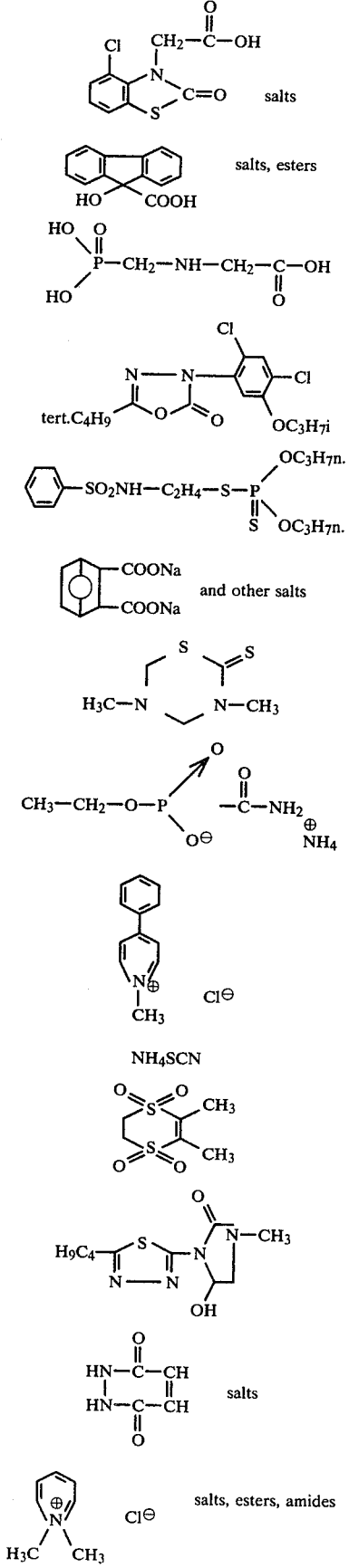

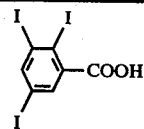

It is also advantageous to apply the compounds of the invention either alone or in combination with other herbicides, in admixture with other crop protection agents, for example agents for combatting pest or phytopathogenic fungi or bacteria. Of further interest is the fact that the compounds of the invention may be mixed with solutions of mineral fertilizers used to eliminate trace element or nutritional deficiencies.

Spreader-stickers and non-phytothoxic oils may be added to the compounds of the invention to ensure that they take effect.

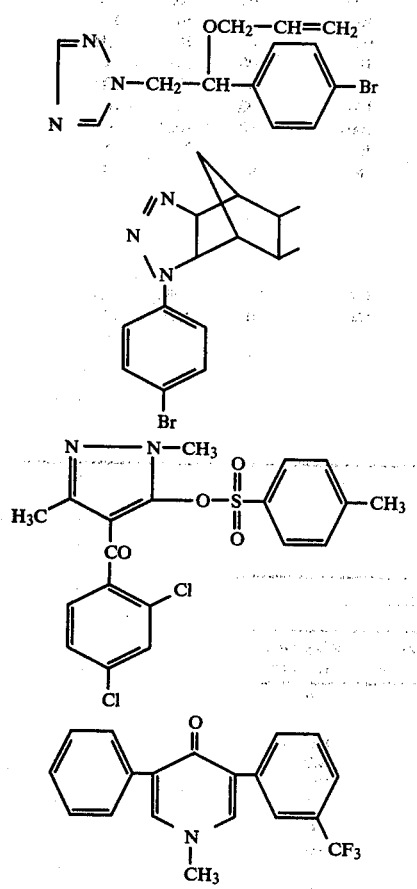

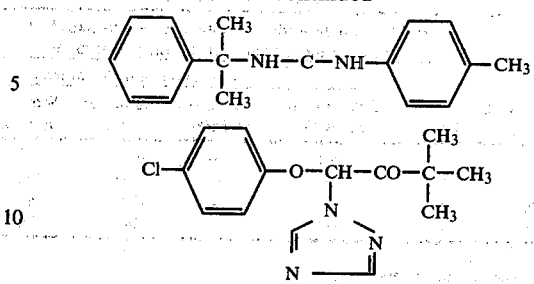

TABLE 1

| List of test plants | |
|---|---|
| Botanical name | English term |
| Abutilon theoprasti | velvet leaf |
| Amaranthus retroflexus | redroot pigweed |
| Carthamus tinctorius | safflower |
| Chenopodium album | lambsquarters (goosefoot) |
| Centaurea cyanus | cornflower |
| Cynodon dactylon | Bermudagrass |
| Cyperus difformis | smallflower umbrellaplant |
| Datura stramonium | Jimsonweed |
| Daucus carota | carrots |
| Echinochloa crus galli | barnyardgrass |
| Euphorbia geniculata | Southamerican member of the spurge family |
| Galium aparine | catchweed bedstraw |
| Helianthus annuus | sunflower |
| Ipomoea spp. | morningglory |
| Lamium purpureum | red deadnettle |
| Lolium multiflorum | annual raygrass |
| Matricaria spp. | chamomile |
| Mercurialis annua | annual mercury |
| Pisum sativum | English peas |
| Polygonum percicaria | ladystumb |
| Polygonum aviculare | prostrate knotweed |
| Raphanus raphanistrum | wild radish |
| Sesbania exaltata | hemp sesbania |
| Setaria spp. | foxtail spp. |
| Sida spinosa | teaweed (prickly sida) |
| Sinapis alba | white mustard |
| Sinapis arvensis | yellow charlock |
| Solanum nigrum | black nightshade |
| Sorghum bicolor | Sorghum |
| Sorghum halepense | Johnsongrass |
| Stellaria media | chickweed |
| Triticum aestivum | wheat |
| Xanthium pensylvanicum | common cocklebur |
| Zea mays | Indian corn |
| Alopecurus myosuroides | slender foxtail |
| Arachis hypogaea | peanut (groundnuts) |
| Fragaria vesca | strawberries |
| Gossypium hirsutum | cotton |
| Lamium amplexicaule | henbit |
| Portulaca oleracea | purslane |

TABLE 2

Herbicidal action of compounds on unwanted plants; preemergence treatment in the greenhouse

| Compound no. | kg/ha | Echinochloa crus galli | Euphorbia geniculata | Ipomoea spp. | Solanum nigrum | Sorghum halepense |
|---|---|---|---|---|---|---|
| 14 | 4.0 | 100 | 75 | 85 | 95 | 85 |
| 68 | 2.0 | 70 | 100 | 93 | — | 70 |
| 106 | 4.0 | 100 | 100 | 100 | 40 | 100 |
| 144 | 4.0 | 100 | 100 | 100 | 80 | 75 |
| 149 | 4.0 | 100 | 100 | 90 | 90 | 75 |
| 113 | 4.0 | 60 | — | 75 | 50 | 60 |
| | | Setaria spp. | | | | |
| 29 | 4.0 | 40 | — | 95 | 90 | 20 |

TABLE 2-continued

Herbicidal action of compounds on unwanted plants; preemergence treatment in the greenhouse

| Compound no. | kg/ha | Echinochloa crus galli | Euphorbia geniculata | Ipomoea spp. | Solanum nigrum | Sorghum halepense |
|---|---|---|---|---|---|---|
| 59 | 4.0 | 100 | — | 100 | 95 | 90 |
| 80 | 4.0 | 100 | — | 100 | 95 | 100 |
| 89 | 4.0 | 100 | — | 100 | 95 | 70 |
| 69 | 4.0 | 100 | — | 100 | 75 | 95 |

0 = no damage
100 = plants completely destroyed

TABLE 3

Herbicidal action; postemergence treatment in the greenhouse

| Compound no. | | kg/ha | Abutilon theophrasti | Echinochloa crus galli | Datura stramonium | Setaria spp. | Sida spinosa | Solanum nigrum |
|---|---|---|---|---|---|---|---|---|
| 29 | | 1.0 | 100 | 0 | 100 | 100 | 100 | 100 |
|  | | 2.0 | 100 | 30 | 100 | 100 | 100 | 100 |
| 59 | | 1.0 | 100 | 40 | 40 | — | 50 | 40 |
|  | | 2.0 | 100 | 65 | 60 | — | 70 | 100 |
| 80 | | 1.0 | 100 | — | 40 | 100 | 20 | 50 |
|  | | 2.0 | 100 | 75 | 100 | 100 | 100 | 100 |
| 89 | | 1.0 | 100 | 75 | 100 | 100 | 80 | 100 |
|  | | 2.0 | 100 | 75 | 100 | 100 | 100 | 100 |
| prior art A | 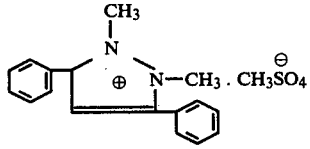 | 1.0 | 15 | 0 | 32 | 0 | 7 | 65 |
|  | | 2.0 | 18 | 0 | 48 | 20 | 25 | 70 |
| prior art B | 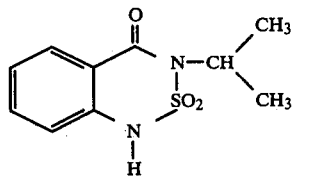 | 1.0 | 100 | 0 | 100 | 0 | 100 | 100 |
|  | | 2.0 | 100 | 0 | 100 | 30 | 100 | 100 |

0 = no damage
100 = plants completely destroyed

TABLE 4

Herbicidal action; postemergence application in the greenhouse

| Compound no. | kg/ha | Centaurea cyanus | Echinochloa crus galli | Galium aparine | Ipomoea spp. | Lolium multiflorum | Polygonum aviculare |
|---|---|---|---|---|---|---|---|
| 67 | 3.0 | 100 | 100 | 0 | 100 | 100 | 0 |
| 15 | 3.0 | 100 | 100 | 100 | 100 | 100 | 0 |
| 71 | 3.0 | 100 | 100 | 30 | 100 | 100 | 100 |
| 70 | 3.0 | 100 | 100 | 30 | 100 | 100 | 100 |
| 31 | 3.0 | 50 | 100 | 50 | 100 | 0 | 100 |
| 77 | 3.0 | 100 | — | 50 | 100 | 50 | 0 |
| 161 | 3.0 | 100 | 100 | 100 | 60 | 100 | 100 |
| 115 | 3.0 | 100 | 50 | 0 | 100 | 100 | 100 |
| 132 | 3.0 | 50 | 100 | 0 | 0 | 100 | — |
| 157 | 3.0 | 100 | 100 | 100 | 100 | 70 | 0 |
| 160 | 3.0 | 100 | 100 | 70 | 100 | 100 | 100 |
| 154 | 3.0 | 100 | 100 | 100 | 100 | 70 | 0 |
| 105 | 3.0 | 100 | 100 | 0 | 100 | 100 | 30 |
| 164 | 3.0 | 100 | 70 | 100 | 100 | 100 | 30 |
| 165 | 3.0 | 100 | 100 | 50 | 100 | 100 | 100 |
| 162 | 3.0 | 100 | 100 | 100 | 100 | 100 | 30 |
| 21 | 3.0 | 100 | 100 | 0 | 100 | 70 | 0 |
| 100 | 3.0 | 100 | 80 | 0 | 100 | 100 | — |
| 159 | 3.0 | 100 | 90 | 100 | 100 | 100 | 100 |
| 166 | 3.0 | 100 | 40 | 70 | 90 | 95 | — |
| 72 | 3.0 | 100 | 40 | 20 | 70 | 95 | — |
| 204 | 3.0 | 40 | 100 | 40 | 0 | 90 | — |
| 158 | 3.0 | 100 | 40 | 95 | 40 | 100 | — |
| 10 | 3.0 | 100 | 80 | 100 | 100 | 100 | — |
| 111 | 3.0 | 40 | 20 | 100 | 40 | 100 | — |
| 187 | 3.0 | 20 | 40 | 100 | 90 | 100 | — |
| 101 | 3.0 | 100 | 40 | 100 | 100 | 100 | — |

TABLE 4-continued

Herbicidal action; postemergence application in the greenhouse

| Compound no. | kg/ha | Centaurea cyanus | Echinochloa crus galli | Galium aparine | Ipomoea spp. | Lolium multiflorum | Polygonum aviculare |
|---|---|---|---|---|---|---|---|
| 221 | 3.0 | 90 | 0 | 90 | 0 | 0 | — |
| 109 | 3.0 | 80 | 40 | 100 | 100 | 100 | — |
| 168 | 3.0 | 100 | 100 | 40 | 0 | 100 | 0 |
| 222 | 3.0 | 100 | 60 | 100 | 95 | — | — |
| 185 | 3.0 | 100 | 35 | 95 | 95 | — | — |

0 = no damage
100 = completely destroyed

TABLE 5

Herbicidal action; postemergence treatment in the open

| Compound no. | kg/ha | Chenopodium album | Matricaria spp. | Polygonum convolvulus | Polygonum persicaria | Raphanus raphanistrum/ Sinapis arvensis | Stellaria media |
|---|---|---|---|---|---|---|---|
| 14 | 2.0 | 80 | 20 | 30 | — | 70 | 70 |
|  | 4.0 | 90 | 40 | 50 | — | 80 | 95 |
| 194 | 2.0 | 98 | 68 | 70 | 65 | 80 | 98 |
|  | 4.0 | 100 | 88 | 95 | 95 | 98 | 100 |
| 68 | 2.0 | 100 | 90 | — | 75 | 85 | 100 |
|  | 4.0 | 100 | 98 | — | 80 | 90 | 100 |
| 82 | 2.0 | 98 | 50 | 90 | 60 | 80 | 95 |
|  | 4.0 | 100 | 95 | 100 | — | 100 | 100 |
| 106 | 2.0 | 100 | 65 | 90 | — | 90 | 85 |
|  | 4.0 | 100 | 90 | 100 | — | 100 | 95 |
| 144 | 2.0 | 100 | 60 | 95 | — | 95 | 100 |
|  | 4.0 | 100 | 90 | 100 | — | 100 | 100 |
| 149 | 2.0 | 100 | 60 | 100 | — | 100 | 100 |
|  | 4.0 | 100 | 80 | 100 | — | 100 | 100 |
| 123 | 2.0 | 100 | 15 | — | 75 | — | 95 |
|  | 4.0 | 100 | 20 | — | 90 | — | 100 |
| 30 | 2.0 | 100 | 20 | — | 80 | — | 100 |
|  | 4.0 | 100 | 40 | — | 100 | — | 100 |
| B prior art | 2.0 | 100 | 100 | 80 | 40 | 100 | 100 |
|  | 4.0 | 100 | 100 | 90 | 100 | 100 | 100 |
| prior art | 2.0 | 50 | 22 | 20 | 30 | — | — |
|  | 4.0 | 88 | 57 | 95 | 62 | 100 | 83 |
| A prior art | 2.0 | 90 | 90 | 60 | — | 60 | 40 |
|  | 4.0 | 95 | 100 | 90 | — | 80 | 60 |

Structure A:
$O_2N$—C₆H₂(NO₂)(O—CO—CH₃)(CH(C₂H₅)CH₃)

(Prior art compound A: a benzene ring with two NO₂ groups, an O—CO—CH₃ group, and a CH(C₂H₅)CH₃ substituent)

0 = no damage
100 = plants completely destroyed

TABLE 6

Herbicidal action in Bermuda grass; postemergence application in the greenhouse

| Compound no. | kg/ha | Cynodon dactylon | Amaranthus retroflexus from rhizomes (Bermuda grass) | Cyperus difformis | Mercurialis annua |
|---|---|---|---|---|---|
| 14 | 1.0 | 10 | 100 | 93 | 98 |
|  | 2.0 | — | 100 | 98 | 98 |
| 145 | 1.0 | 0 | — | 100 | 100 |
|  | 2.0 | 0 | — | — | 100 |
| 82 | 1.0 | 10 | 25 | 100 | 100 |
|  | 2.0 | 20 | 40 | — | 100 |
| B prior art | 1.0 | 0 | 70 | 100 | 36 |
|  | 2.0 | — | 100 | 100 | 56 |

0 = no damage
100 = plants completely destroyed

TABLE 7

Selective herbicidal action in peas; postemergence treatment in the greenhouse

| Compound no. | kg/ha | Pisum sativum | Ipomoea spp. | Matricaria spp. | Setaria spp. | Sinapis alba | Stellaria media |
|---|---|---|---|---|---|---|---|
| 113 | 1.0 | 0 | 40 | 100 | 30 | — | — |
|  | 2.0 | 10 | 75 | 100 | 100 | — | — |
| 30 | 1.0 | 0 | 60 | 0 | 40 | 100 | 100 |
|  | 2.0 | 10 | 65 | 0 | 75 | 100 | 100 |
| 68 | 1.0 | 2 | 95 | 100 | 98 | 100 | 100 |
|  | 2.0 | 4 | 99 | 100 | 98 | 100 | 100 |
| 14 | 1.0 | 12 | 90 | 7 | 98 | 90 | 95 |
|  | 2.0 | 20 | 100 | 7 | 98 | 95 | 95 |
| 69 | 1.0 | 0 | 100 | 100 | 100 | 100 | 100 |
|  | 2.0 | 0 | 100 | 100 | 100 | 100 | 100 |
| B prior art | 1.0 | 10 | 43 | 100 | 0 | 98 | 98 |
|  | 2.0 | — | 55 | 100 | 30 | 98 | 98 |
| C prior art | 1.0 | 15 | 0 | 20 | — | 80 | 90 |
|  | 2.0 | 28 | — | 20 | — | 100 | 100 |

0 = no damage
100 = plants completely destroyed

TABLE 8

Selective herbicidal action in safflower; postemergence application in the greenhouse

| Compound no. | kg/ha | Carthamus tinctorius | Amaranthus retroflexus | Euphorbia geniculata | Mercurialis annua | Sesbania exaltata | Sida spinosa | Solanum nigrum | Xanthium pensylvani |
|---|---|---|---|---|---|---|---|---|---|
| 144 | 1.0 | 0 | 100 | 100 | 100 | 100 | 100 | 100 | 100 |
|  | 2.0 | 0 | 100 | 100 | 100 | 100 | 100 | 100 | 100 |
| 28 | 1.0 | — | 100 | 50 | 30 | 98 | — | — | — |
|  | 2.0 | 0 | 100 | 70 | 100 | 95 | — | — | — |
| 17 | 1.0 | — | 0 | 60 | 100 | 90 | — | — | 100 |
|  | 2.0 | 0 | 0 | 70 | 100 | 100 | — | — | 100 |
| 14 | 1.0 | 0 | 100 | 90 | 98 | 95 | 100 | 82 | 89 |
|  | 2.0 | 0 | 100 | 96 | 98 | 100 | 100 | 100 | 98 |
| 30 | 1.0 | 0 | 88 | 85 | 100 | 95 | — | 20 | 30 |
|  | 2.0 | 0 | 90 | 85 | 100 | 95 | — | 100 | 30 |

0 = no damage
100 = plants completely destroyed

TABLE 9

Selective herbicidal action; postemergence treatment in the greenhouse

Basic molecule 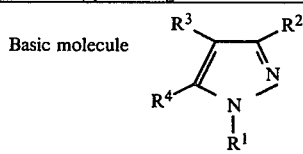

| Compound no. | R[1] | R[2] | R[3] | R[4] | kg/ha | Daucus carota | Helianthus annuus | Sorghum bicolor | Triticum aestivum | Zea mays |
|---|---|---|---|---|---|---|---|---|---|---|
| 30 |  |  |  |  | 1.0 | 0 | 0 | 0 | 10 | 10 |
|  |  |  |  |  | 2.0 | 0 | 10 | 10 | 23 | 10 |
| 41 |  |  |  |  | 1.0 | — | — | — | — | 10 |
|  |  |  |  |  | 2.0 | — | — | — | 0 | 20 |
| 144 |  |  |  |  | 1.0 | — | 15 | — | 0 | 0 |
|  |  |  |  |  | 2.0 | — | 20 | — | — | 0 |
| 149 |  |  |  |  | 1.0 | — | 10 | — | — | 0 |
|  |  |  |  |  | 2.0 | — | 30 | — | — | 0 |
| prior art D | CH$_3$ | —CH$_3$ | ![structure] | ![structure] | 1.0 | — | — | — | 0 | — |
|  |  |  |  |  | 2.0 | — | — | — | 0 | — |
| prior art E | CH$_3$ | —CH$_3$ | ![structure] | —OH | 1.0 | — | — | — | — | — |
|  |  |  |  |  | 2.0 | — | — | — | — | — |
| A prior |  |  |  |  | 1.0 | — | — | 5 | 0 | 10 |
|  |  |  |  |  | 2.0 | — | — | 5 | 0 | 10 |

TABLE 9-continued

Selective herbicidal action; postemergence treatment in the greenhouse

Basic molecule: pyrazole with R¹, R², R³, R⁴ substituents

| | | | | | | | | | | |
|---|---|---|---|---|---|---|---|---|---|---|
| art C | | | | 1.0 | 30 | 100 | 0 | 12 | 10 | |
| prior art | | | | 2.0 | 35 | 100 | 10 | 18 | 15 | |

| | | | | Test plants and % damage | | | | | | |
|---|---|---|---|---|---|---|---|---|---|---|
| Compound no. | Echinochloa crus galli | Euphorbia geniculata | Ipomoea spp. | Lamium purpureum | Mercurialis annua | Polygonum persicaria | Sesbania exaltata | Setaria spp. | Sinapis alba | Stellaris media |
| 30 | 20 | 85 | 60 | 80 | 100 | 100 | 95 | 40 | 100 | 100 |
|  | 27 | 85 | 65 | 80 | 100 | 100 | 95 | 75 | 100 | 100 |
| 41 | 10 | 40 | 52 | 10 | 100 | 60 | 60 | 20 | 100 | — |
|  | 10 | 50 | 100 | 20 | 100 | 90 | 60 | 40 | 100 | — |
| 144 | 70 | 100 | 95 | 95 | 100 | — | 100 | 100 | 100 | — |
|  | 100 | 100 | 95 | 95 | 100 | — | 100 | 100 | — | — |
| 149 | 100 | 100 | 90 | 95 | 100 | — | 100 | 95 | 100 | — |
|  | 100 | 100 | 100 | 95 | 100 | — | 100 | 95 | 100 | — |
| prior art D | 70 | — | — | — | — | — | — | — | 0 | — |
|  | 80 | — | 20 | — | 30 | — | — | — | 25 | — |
| prior art E | 10 | — | 0 | 0 | 0 | — | — | — | 15 | 60 |
|  | — | — | 0 | 0 | 0 | — | — | — | 45 | 60 |
| A | 0 | 100 | 13 | 0 | 10 | — | 40 | 0 | 0 | 30 |
| prior art C | 0 | 100 | 15 | 0 | 50 | — | 50 | 20 | 0 | 45 |
|  | 0 | — | 0 | 100 | — | — | — | — | 80 | 90 |
| prior art | 0 | — | — | 100 | — | — | — | — | 100 | 100 |

0 = no damage
100 = plants completely destroyed

TABLE 10

Herbicidal action in strawberries; postemergence treatment in the greenhouse

| Compound no. | kg/ha | Fragaria vesca | Lamium amplexicaure | Mercurialis annua | Solanum nigrum | Stellaria madia |
|---|---|---|---|---|---|---|
| 30 | 2.0 | 20 | 100 | 100 | 100 | 100 |
| 14 | 1.0 | 0 | 100 | 98 | 100 | 100 |
| 82 | 0.5 | 0 | 30 | 100 | 100 | 100 |
| 144 | 1.0 | 20 | 60 | 100 | — | 100 |
| 123 | 1.0 | 10 | 60 | 100 | 100 | 100 |
| 113 | 1.0 | 20 | 100 | 100 | — | 100 |
| 194 | 1.0 | 0 | 100 | 100 | 100 | 100 |

0 = no damage
100 = plants completely destroyed

TABLE 11

Herbicidal action in peanuts and cotton; postemergence application in the greenhouse

| Compound no. | kg/ha | Arachia hypognea | Gossypium hirsutum | Alopocurus myosuroides | Amaranthus retroflexus | Chenopodium album | Echinochloa crus galli | Ipomoea spp. | Portulaca oleracea | Sesbania exaltata | Solanum nigrum |
|---|---|---|---|---|---|---|---|---|---|---|---|
| 67 | 1.0 | 10 | 0 | 90 | 100 | 100 | 60 | 100 | 100 | 100 | 100 |
| 68 | 0.5 | 10 | — | 90 | 100 | 100 | 70 | 75 | 100 | 95 | 100 |
| 69 | 0.5 | 10 | 0 | 95 | 50 | 100 | 40 | 75 | 100 | 60 | 100 |
| 70 | 1.0 | 0 | 0 | 95 | 50 | 90 | — | 60 | 100 | 60 | 100 |
| 198 | 1.0 | 20 | 20 | 95 | 50 | 100 | 95 | 90 | 100 | 100 | 100 |
| 77 | 2.0 | 0 | 10 | 95 | — | 90 | 100 | 60 | 100 | 95 | 100 |
| 21 | 1.0 | 0 | 0 | 60 | — | 100 | — | 100 | — | — | — |
| 165 | 0.5 | 15 | 0 | 85 | 100 | 100 | — | — | 100 | — | 40 |
| 106 | 0.5 | 10 | 15 | 90 | 100 | 90 | — | — | 70 | — | — |
| 153 | 2.0 | 0 | 20 | — | 100 | 100 | 40 | — | 100 | — | 100 |
| 154 | 0.5 | 5 | 20 | 80 | 100 | 100 | 70 | 80 | 100 | 95 | 100 |
| 31 | 2.0 | 0 | 0 | — | 100 | 90 | — | 100 | 100 | 70 | — |
| 160 | 1.0 | 0 | 0 | 95 | 100 | 100 | 100 | — | 100 | 100 | 100 |
| 80 | 1.0 | 5 | 5 | — | — | — | 100 | 50 | 100 | 100 | — |
| 161 | 0.5 | 15 | 0 | 100 | — | 100 | 90 | — | 100 | 100 | 100 |

0 = no damage
100 = plants completely destroyed

TABLE 12

Herbicidal action on weeds; postemergence application in the greenhouse

| Compound no. | kg/ha | Alopecurus myosuroides | Ipomoea spp. | Sesbania exaltata | Sida spinosa | Xanthium pensylvanicum |
|---|---|---|---|---|---|---|
| 29 | 1.0 | 95 | 83 | 100 | 100 | 100 |
|  | 2.0 | 100 | 88 | 100 | 100 | 100 |
| 161 | 2.0 | 100 | 85 | 100 | 100 | 60 |
| 82 | 2.0 | 98 | 82 | 100 | 60 | 100 |
| 162 | 1.0 | 94 | 65 | 90 | — | 90 |
|  | 2.0 | 98 | 65 | 100 | — | 90 |
| 89 | 1.0 | 90 | 100 | 80 | 60 | 40 |
|  | 2.0 | 95 | 100 | 100 | 100 | 90 |
| 164 | 2.0 | 95 | 90 | 100 | — | 80 |
| 105 | 2.0 | 95 | — | 100 | 90 | 80 |
| 68 | 2.0 | 94 | 93 | 98 | 100 | 50 |
| 71 | 2.0 | 95 | 100 | 100 | 100 | — |
| 106 | 2.0 | 95 | 90 | 80 | 80 | — |
| 165 | 2.0 | 95 | 100 | 100 | 100 | — |
| 144 | 1.0 | 50 | 95 | 100 | 100 | 100 |
|  | 2.0 | 80 | 95 | 100 | 100 | 100 |
| 149 | 1.0 | 70 | 90 | 100 | 100 | 40 |
|  | 2.0 | 80 | 100 | 100 | 100 | 100 |

0 = no damage
100 = plants completely destroyed

TABLE 13

Selective herbicidal action; postemergence application in the greenhouse

| Compound no. | kg/ha | Triticum aestivum | Zea mays | Amaranthus retroflexus | Chenopodium album | Euphorbia geniculata | Matricaria spp. | Sinapis alba | Sesbania exaltata | Solanum nigrum |
|---|---|---|---|---|---|---|---|---|---|---|
| 202 | 0.5 | 5 | 5 | 100 | 100 | 100 | 100 | 100 | 100 | 100 |
|  | 1.0 | 10 | 12 | 100 | 100 | 100 | 100 | 100 | 100 | 100 |
| 151 | 0.5 | 0 | — | — | 100 | 100 | 100 | 100 | 90 | 100 |
|  | 1.0 | 0 | — | — | 100 | 100 | 100 | 100 | 100 | 100 |

EXAMPLE 11

9 parts by weight of compound 1 is mixed with 1 parts by weight of N-methyl-α-pyrrolidone. A mixture is obtained which is suitable for application in the form of very fine drops.

EXAMPLE 12

20 parts by weight of compound 2 is dissolved in a mixture consisting of 80 parts by weight of xylene, 10 parts by weight of the adduct of 8 to 10 moles of ethylene oxide to 1 mole of oleic acid-N-monoethanolamide, 5 parts by weight of the calcium salt of dodecylbenzenesulfonic acid, and 5 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 13

20 parts by weight of compound 3 is dissolved in a mixture consisting of 40 parts by weight of cyclohexanone, 30 parts by weight of isobutanol, 20 parts by weight of the adduct of 7 moles of ethylene oxide to 1 mole of isooctylphenol, and 10 parts by weight of the adduct of 40 moles of ethylene oxide to 1 mole of castor oil. By pouring the solution into 100,000 parts by weight of water and finely distributing it therein, an aqueous dispersion is obtained containing 0.02% by weight of the active ingredient.

EXAMPLE 14

20 parts by weight of compound 1 is dissolved in a mixture consisting of 25 parts by weight of cyclohexanol, 65 parts by weight of a mineral oil fraction having a boiling point between 210° C. and 280° C., and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 15

20 parts by weight of compound 2 is well mixed with 3 parts by weight of the sodium salt of diisobutylnaphthalene-α-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquid is obtained containing 0.1% by weight of the active ingredient.

EXAMPLE 16

3 parts by weight of compound 3 is intimately mixed with 97 parts by weight of particulate kaolin. A dust is obtained containing 3% by weight of the active ingredient.

EXAMPLE 17

30 parts by weight of compound 4 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE 18

40 parts by weight of compound 1 is intimately mixed with 10 parts of the sodium salt of a phenolsulfonic acid-urea-formaldehyde condensate, 2 parts of silica gel and 48 parts of water. Dilution in 100,000 parts by weight of water gives an aqueous dispersion containing 0.04 wt% of active ingredient.

EXAMPLE 19

20 parts of compound 2 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

We claim:
1. A pyrazole of the formula

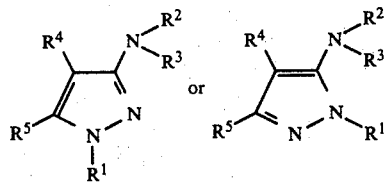
where
- $R^1$ is hydrogen,
- $R^2$ is hydrogen or lower alkyl,
- $R^3$ is n-propyl, isopropyl, n-butyl, sec-butyl, isobutyl, tert-butyl, 3-methyl-2-butyl, pentyl-2 or pentyl-3 or one of said groups substituted by lower alkoxy or is a 5-, 6-, or 7-membered cycloalkyl,
- $R^4$ is methoxycarbonyl, and
- $R^5$ is hydrogen or methyl, and the agriculturally acceptable acid addition salts thereof.
* * * * *